United States Patent
Hernandez

(10) Patent No.: US 12,070,612 B2
(45) Date of Patent: Aug. 27, 2024

(54) SYSTEM AND METHOD FOR ALIGNMENT OF A WIRELESS CHARGER TO AN IMPLANTABLE MEDICAL DEVICE

(71) Applicant: Advanced Neuromodulation Systems Inc., Plano, TX (US)

(72) Inventor: Luis Ortiz Hernandez, Plano, TX (US)

(73) Assignee: Advanced Neuromodulation Systems Inc., Plano, TX (US)

( * ) Notice: Subject to any disclaimer, the term of this patent is extended or adjusted under 35 U.S.C. 154(b) by 827 days.

(21) Appl. No.: 17/135,725

(22) Filed: Dec. 28, 2020

(65) Prior Publication Data

US 2022/0203103 A1    Jun. 30, 2022

(51) Int. Cl.
  *A61N 1/378* (2006.01)
  *H02J 50/10* (2016.01)
  *H02J 50/90* (2016.01)

(52) U.S. Cl.
  CPC ............ *A61N 1/3787* (2013.01); *H02J 50/10* (2016.02); *H02J 50/90* (2016.02)

(58) Field of Classification Search
  CPC ........ A61N 1/3787; H02J 50/10; H02J 50/90; H02J 2310/23
  See application file for complete search history.

(56) References Cited

U.S. PATENT DOCUMENTS

| | | | |
|---|---|---|---|
| 5,411,537 A | 5/1995 | Munshi et al. | |
| 5,702,431 A | 12/1997 | Wang et al. | |
| 7,177,691 B2 | 2/2007 | Meadows et al. | |
| 7,932,696 B2 * | 4/2011 | Peterson | A61N 1/3787 320/114 |
| 8,335,569 B2 * | 12/2012 | Aghassian | A61N 1/37217 607/30 |
| 8,694,117 B2 | 4/2014 | Aghassian et al. | |
| 8,731,682 B2 | 5/2014 | Winstrom | |
| 9,209,634 B2 | 12/2015 | Cottrill et al. | |
| 9,339,660 B2 * | 5/2016 | Feldman | A61N 1/3787 |
| 9,968,795 B2 | 5/2018 | Imran et al. | |
| 10,105,541 B2 | 10/2018 | Kishawi et al. | |
| 10,632,318 B2 | 4/2020 | Stouffer | |
| 2005/0288739 A1 | 12/2005 | Hassler et al. | |

(Continued)

OTHER PUBLICATIONS

Static Fields, 2023, Environmental Protection Agency (Year: 2023).*

*Primary Examiner* — Catherine M Voorhees
(74) *Attorney, Agent, or Firm* — Jessica Smith; LOZA & LOZA, LLP

(57) ABSTRACT

A magnetic field sensor is positioned in proximity to a charging coil in an implantable medical device (IMD). An external device for charging the IMD includes a primary coil and a magnet positioned in proximity to the primary coil. The magnetic field sensor in the IMD detects a static magnetic field of the magnet and provides measurements proportional to the static magnetic field along three axes. These measurements of the static magnetic field are used to determine whether the external device is aligned with the IMD for charging. These measurements of the static magnetic field may also be processed to determine a position of the charger device relative to the IMD in three dimensions. When misaligned, a direction may be generated for a user to reposition the charger device to improve alignment.

14 Claims, 18 Drawing Sheets

(56) References Cited

U.S. PATENT DOCUMENTS

| | | | |
|---|---|---|---|
| 2012/0256494 A1* | 10/2012 | Kesler | H02J 50/40 |
| | | | 307/104 |
| 2018/0272139 A1* | 9/2018 | Stouffer | A61N 1/3787 |
| 2018/0352349 A1* | 12/2018 | Fung | H04R 25/606 |
| 2019/0105496 A1 | 4/2019 | Min et al. | |
| 2019/0247669 A1* | 8/2019 | Nielsen | H02J 50/10 |
| 2020/0084822 A1 | 3/2020 | Oza et al. | |
| 2020/0188680 A1 | 6/2020 | Aghassian et al. | |
| 2020/0324126 A1 | 10/2020 | Winstrom | |

* cited by examiner

SYSTEM AND METHOD FOR ALIGNMENT OF A WIRELESS CHARGER TO AN IMPLANTABLE MEDICAL DEVICE

FIELD

The present disclosure relates generally to an implantable medical device with a rechargeable battery and more particularly, to a system and method for alignment of an external wireless charger to the implantable medical device for recharging the battery.

BACKGROUND

The statements in this section provide a description of related art and are not admissions of prior art. No admission is made that the related art is publicly available or known to others besides the inventors.

An implantable medical device (IMD) is partially or totally introduced, surgically or medically, into the body of a patient, human or non-human. An IMD includes for example, a neurostimulation device for spinal cord stimulation, deep brain stimulation, cortical stimulation, cochlear nerve stimulation, peripheral nerve stimulation, vagal nerve stimulation, sacral nerve stimulation, and others. Such IMDs are configured to be implanted within the patient and include one or more electrodes that deliver electrostimulation to tissue for diagnostic or therapeutic purposes. For example, a neurostimulation device may be a spinal cord stimulator (SCS) that treats chronic pain by delivering stimulation pulses to a patient's spinal cord that induce paresthesia in regions of the patient's body. Other examples of IMDs include pacemakers for treating cardiac arrhythmia, defibrillators for treating cardiac fibrillation, cochlear stimulators for treating deafness, retinal stimulators for treating blindness, or muscle stimulators for producing coordinated limb movement or reducing tremors. In addition, IMDs may include any other device configured for implantation in a patient.

An electrically operated IMD implanted in the patient needs a reliable power source. Some electrically operated IMDs are powered by a primary cell (commonly referred to as a non-rechargeable battery). When the battery of such an IMD is depleted, the device must be removed from the patient's body such that its battery can be replaced or a new IMD with a new battery may be implanted. To avoid removal of an IMD, other electrically operated IMDs include secondary cells (commonly referred to as rechargeable batteries). The rechargeable battery of such an IMD is recharged using a non-implanted or external wireless charger device. For example, the external charger device includes an inductive coil that enables power to be wirelessly transferred, through the patient's skin, from the charger device to an inductive coil in the IMD to charge the rechargeable battery.

In general, to effectively recharge the IMD, the external charger device needs to be positioned over the skin of the patient and within a certain range and alignment of the IMD. Improper positioning of the external charger device may trigger false detection of the presence of the IMD and start false charging. The improper positioning may also lead to inefficient charging time, high charging power consumption or even generation of heat on undesired metal surfaces of the IMD. However, it is difficult for a patient to determine proper alignment of the charger device with the IMD since the IMD is implanted under the skin of the patient.

Known systems for determining alignment use proximity sensors to detect whether the IMD and the charger device are within a predetermined range. However, such proximity sensors are not able to determine a positional relationship of the charger device with respect to the IMD in two or three dimensions or detect an alignment of the inductive coils in the charger device with the inductive coils in the IMD along two or three dimensions. Thus, there is a need for an improved system and method for determining an alignment of the external charger device with respect to the IMD under the skin of the patient for charging of the secondary cell. Other advantages of embodiments of the systems and methods are described herein or are apparent from implementations thereof.

SUMMARY

The following presents a summary of the disclosed subject matter in order to present some aspects of the disclosed subject matter.

In one aspect, a system for wirelessly providing power to an implantable medical device includes an external charger device and an external user device. These devices may be separate or incorporated into a same device. The external charger device includes a primary coil configured to wirelessly transfer power to a charging coil in the IMD and at least one magnet having a static magnetic field, wherein the at least one magnet is positioned in proximity to the primary coil. The external user device includes a transceiver configured to communicate with the IMD using a wireless protocol and at least one processing circuit including at least one processing device and at least one memory device, wherein the at least one memory device stores instructions that, when executed by the at least one processing device, causes the second external device the processing circuitry is configured to obtain a magnetic field measurement along each of three axes, wherein each of the magnetic field measurements is a value proportional to a static magnetic field detected along one of the three axes by at least one magnetic field sensor in the IMD and determine a relative position in three dimensions of the external charger device to the IMD using the magnetic field measurements.

In a second aspect, an implantable medical device (IMD) includes a charging coil configured to wirelessly receive power from a first external device and at least one magnetic field sensor positioned in proximity to the charging coil, wherein the magnetic field sensor is configured to measure a static magnetic field. A controller is configured to obtain magnetic field measurements of the static magnetic field in each of three dimensions from the at least one magnetic field sensor and generate one or more messages to a second external device including the magnetic field measurements in each of the three dimensions.

In a third aspect, an external system for wirelessly providing power to an implantable medical device (IMD) includes a plurality of primary coils configured to wirelessly transfer power to a charging coil in the IMD; a plurality of magnets, wherein each magnet of the plurality of magnets is positioned more proximal to a different one of the plurality of primary coils; and a transceiver configured to communicate with the IMD using a wireless protocol. At least one processing circuit is configured to obtain magnetic field measurements in each of three dimensions, wherein each of the magnetic field measurements is a value proportional to a magnetic field detected by at least one magnetic field sensor in the IMD; select one of the plurality of primary coils for wireless transfer of power to the charging coil in the IMD; and determine a relative position in three dimensions of the external device to the IMD using the magnetic field measurements.

In one or more of the above aspects, the external user device determines a direction to move the external charger device with respect to a patient's skin to improve alignment of the primary coil in the external charger device to the charging coil in the IMD.

In one or more of the above aspects, the external user device generates an indication to move the external charger device in the determined direction, wherein the indication is a visual graphical user interface (GUI) or an audible indication.

In one or more of the above aspects, the external user device determines a direction to tilt a portion of the external charger device with respect to a patient's skin such that the primary coil in the external charger device and the charging coil in the IMD are relatively more parallel.

In one or more of the above aspects, the external user device generates an indication to tilt the portion of the external charger device with respect to the patient's skin, wherein the indication is a visual graphical user interface (GUI) or an audible indication.

In one or more of the above aspects, the external user device determine to move the external charger device in closer proximity to a patient's skin such that a relative distance from a center of the primary coil in the external charger device and a center of the charging coil in the IMD is decreased.

In one or more of the above aspects, the external user device generates an indication to move the external charger device in closer proximity to a patient's skin, wherein the indication is a visual graphical user interface (GUI) or an audible indication.

In one or more of the above aspects, the external user device determines an alignment of the primary coil to the charging coil when the relative positions in each of three dimensions of the external device to the IMD are within predetermined distance thresholds.

In one or more of the above aspects, the external user device determines an alignment of the primary coil to the charging coil when the magnetic field measurements along the three axes is within predetermined thresholds.

In one or more of the above aspects, the at least one magnetic field sensor is positioned within a circumference of the charging coil and/or the at least one magnetic field sensor is positioned on a central axis of wire windings of the charging coil.

In one or more of the above aspects, the first external device includes a charger device and wherein the second external device includes a patient controller device. The first external device and the second external device may be a same user device.

In one or more of the above aspects, each magnet of the plurality of magnets presents a different polarization towards the at least one magnetic field sensor in the IMD such that a different output of magnetic field measurements is obtained depending on a proximity of each magnet of the plurality of magnets to the at least one magnetic field sensor.

In one or more of the above aspects, one of the plurality of primary coils is selected for wireless transfer of power to the charging coil in the IMD using at least the magnetic field measurements in each of three dimensions.

In one or more of the above aspects, the one of the plurality of primary coils is selected by determining the one of the plurality of primary coils having a greater overlapping surface area to the charging coil in the IMD based on the relative position in three dimensions of the external device to the IMD.

In one or more of the above aspects, a direction to move the external device is determined to improve alignment of the selected one of the plurality of primary coils to the charging coil in the IMD.

In one or more of the above aspects, a direction to angle the external device is determined such that the selected one of the plurality of primary coils and the charging coil are relatively more parallel.

Additional aspects of the invention are set forth, in part, in the detailed description, figures and claims which follow, and in part may be derived from the detailed description, or may be understood by practice of the embodiments. It is to be understood that the description herein is exemplary and explanatory only and is not restrictive of the embodiments as claimed.

BRIEF DESCRIPTION OF THE DRAWINGS

The present disclosure may be better understood, and its numerous features and advantages made apparent to those skilled in the art by referencing the accompanying drawings. The use of the same reference symbols in different drawings may indicate similar, equivalent, or identical components or a different embodiment of a component.

DETAILED DESCRIPTION

The description and drawings merely illustrate the principles of various embodiments. Additional arrangements, although not explicitly described or shown herein, are intended to be included within a scope of the disclosure. Furthermore, examples recited herein are intended for pedagogical purposes to aid in understanding the principles of the embodiments and are not intended to limit the scope to such specifically recited examples. Moreover, statements herein reciting principles, aspects, and embodiments, as well as specific examples thereof, are intended to encompass equivalents thereof.

In one embodiment, a magnetic field sensor is positioned near a charging coil in an implantable medical device (IMD). An external charger device for charging the IMD includes a primary coil and a magnet that is positioned near or within a circumference of the primary coil. The magnetic field sensor in the IMD detects a strength of the magnetic field generated by the magnet in three dimensions, e.g. along the X, Y, and Z axes. The magnetic field sensor then provides a value proportional to the magnetic field strength in the three dimensions. These values of the magnetic field strength are used to determine whether the external charger device is properly aligned with the IMD for charging. When misaligned, one or more audible, visual, or tactile indicators are generated by the external device to signal that the charger device needs to be repositioned. Since the position of the charger device relative to the IMD is determined in three dimensions, the direction of repositioning of the charger device may be indicated to the user in two or three dimensions.

Figure 1:
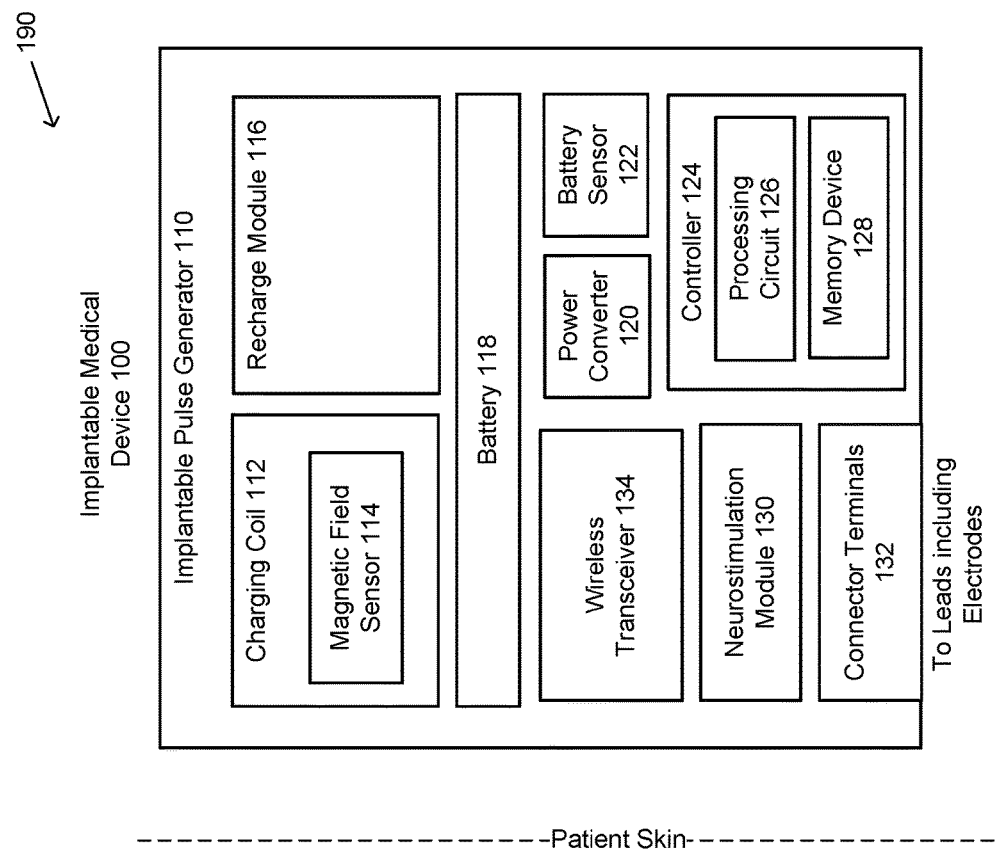
FIG. 1 is a schematic block diagram illustrating selected components of an implantable medical device (IMD) and external devices according to some embodiments.

FIG. 1 is a schematic block diagram illustrating an embodiment of selected components of an implantable medical device (IMD) 100 and external devices 102. The system 190 in FIG. 1 is intended to be exemplary, and in other implementations may include additional or alternative components or devices. In this example, the IMD 102 is an implantable pulse generator (IPG) 110 configured for spinal cord stimulation or deep brain stimulation, though a person of skill in the art will understand that other types of IMDs may also implement the embodiments herein. The IMD is internal to a patient or user, human or non-human.

The IPG 110 includes a charging coil 112 and a magnetic field sensor 114 described in more detail herein. The IPG 110 is also shown as including a recharge module 116, battery 118, power converter 120 and battery sensor 122. The battery 118 is a rechargeable battery such as a lithium ion battery, but is not limited thereto. The recharge module 116 is operable to receive externally generated power through the charging coil 112, and uses the externally generated power to charge the battery 118. The power convertor 120 converts power from the battery 118 for transfer to one or more components of the IPG 110. The battery sensor 122 determines a power level of the battery 118 and provides alerts when the battery 118 is fully charged or when the battery 118 is low on power.

A controller 124 includes at least one processing circuit 126 and at least one memory device 128 and is configured to control the one or more functions of the IPG 110 described herein. The memory device 180 is a non-transitory, processor readable medium that stores programs, code, states, instructions and/or data which when executed or processed by the processing circuit 126, causes the IPG 110 to perform one or more functions described herein.

The IPG 110 further includes a neurostimulation module 130 configured to generate electrical pulses for delivery by electrodes to target neural tissue. The IPG 110 is coupled to the electrodes via one or more leads. The connector terminals 132 couple the leads to the IPG 110. The neurostimulation module 130 delivers electrical pulses in accordance with selected neurostimulation parameters, which can specify a lead, an electrode configuration for the specified lead, and one or more pulse parameters, including, but not limited to, pulse amplitude, pulse width and pulse repetition rate parameters.

A wireless transceiver 134 is configured to communicate to one or more of the external devices 102 using a proprietary wireless protocol or a standard wireless protocol, e.g. such as the wireless Bluetooth™ protocol standard. The wireless transceiver 134 may additionally or alternatively use a wireless far field communication protocol with one or more of the external devices 102, e.g. such as the Medical Implant Communication Service (MICS) standard, which was defined by the U.S. Federal Communications Commission (FCC) and European Telecommunications Standards Institute (ETSI). The MICS standard uses the RF band between 402 and 405 MHz to provide for bi-directional radio communication with implantable medical devices (IMDs), such as the IPG 110. In 2009 the FCC began referring to the RF band between 402 and 405 MHz as being part of the 401 to 406 MHz Medical Device Radio communications (MedRadio) Service band. Accordingly, the RF band between 402 and 405 MHz can be referred to as the MICS/MedRadio band, and the communication standards relating to the MICS/MedRadio band can be referred to as the MICS/MedRadio communication standards. Alternatively, the wireless transceiver 134 can perform wireless RF communications with one or more of the external devices 102 using the Industrial, Scientific, and Medical (ISM) radio bands. The IPG 110 may also perform wireless communication with one or more of the external devices 102 using the 3GPP Release 13, eMTC, NB-IOT or EC-GSM-IoT standards, and in particular the Internet of Medical Things (IoMT) applications of such standards. The use of other standards and frequency bands are also possible.

The IPG 110 may also communicate with the charger device 150 using near field communication, such as reflected impedance modulation, which is sometimes known in the art as Load Shift Keying (LSK) or Amplitude-shift keying (ASK). LSK, which is a particular form of ASK, is a communication scheme which allows simultaneous powering and data transmission through inductive coupling, e.g. of the charging coil 112 with a primary coil 152 of the external charger device 150. A change of the load on the charging coil 112 is reflected onto the primary coil 152 as a varying impedance (i.e., reflected impedance). The near field communication may be used to perform inductive near field communication in noisy RF environments, e.g., as a backup to Bluetooth or other wireless communication implemented by the wireless transceiver 134. Additionally, or alternatively, for security and/or authentication reasons, the near field communication may be used to perform inductive near field communication to initiate a communication session, and then the communication can be switched to higher speed Bluetooth or other communication protocols for the remainder of the communication session.

The IPG 110 typically includes at least one printed circuit board (PCB) with the above various electronic components mounted to the at least one PCB. The one or more PCBs may include the charging coil 112 as well as a second coil for use as an antenna for the wireless transceiver 134. In another embodiment, the charging coil 112 may be wrapped around the PCB including one or more of these components. The various components may be coupled either directly or indirectly via separate buses or via a shared data bus.

The external devices 102 are non-implanted or non-implantable devices and are external to the skin of the patient. The external devices 102 in this example of a system 190 include a charger device 150 and patient controller 170. The patient controller 170 may be a dedicated control device or a non-dedicated user device, such as a smart phone, smart tablet, smart watch, laptop, desktop, or any other external control device configured to control the IPG 110. The patient controller 170 includes a transceiver 172 that is configured to communicate at least with the wireless transceiver 134 of the IPG 110, and may in some embodiments communicate with the charger device 150, using one or more wireless communication protocols, e.g. such as described herein with respect to the wireless transceiver 134 of the IPG 110.

The patient controller application 176 is configured to adjust parameters of the IPG 110 in accordance with a patient's prescribed program. For example, the patient may control a mode of the IPG 110 (Airplane Ready Mode, Surgery Mode or MRI Mode) or a type of therapy program (continuous, intermittent or sleep) or a strength of the stimulation pulses. The patient controller 170 receives the control commands from the patient through the user interface 178 and transmits the control commands to the IPG 110. The user interface 178 may include one or more of a display, keyboard, touchscreen, touchpad, mouse or other such input or output devices. The memory device 180 is a non-transitory, processor readable medium that stores programs, code, states, instructions and/or data which when executed or processed by the processing circuit 174, causes the patient controller 170 to perform one or more functions described herein.

The charger device 150 includes a transceiver 156, processing circuit 158, positioning application 160, user interface 162, power source 164 and memory 166. The transceiver 156 is configured to communicate with the wireless transceiver 134 using one or more wireless communication protocols, e.g. such as described herein with respect to the wireless transceiver 134 of the IPG 110. The memory device 166 is a non-transitory, processor readable medium that stores programs, code, states, instructions and/or data which when executed or processed by the processing circuit 158 enables the charger device 150 to perform one or more functions described herein.

The user interface 162 includes one or more of a display, keyboard, touchscreen, touchpad, mouse or other such input or output devices. The user interface 162 allows a patient or clinician to operate the charger device 150.

The charger device 150 further includes a primary coil 152 configured for power transmission to the charging coil 112 of the IPG 110. Power transmission from the charger device 150 to the IPG 110 occurs wirelessly and transcutaneously through the patient's skin and tissue, via inductive coupling. Such an inductive coupling enables the IPG 110 to receive power from the charger device 150 and recharge the battery 118. More specifically, an alternating current (AC) in the primary coil 152 generates a magnetic field with a fluctuating magnetic field strength. This fluctuating magnetic field in turn induces an AC current in the charging coil 112. The AC current is rectified and smoothed by the recharge module 116 to output a substantially constant DC voltage signal. This substantially constant DC voltage signal is then applied to charge or recharge the battery 118.

In an embodiment, rather than a separate transceiver 156, the charger device 150 may communicate with the IPG 110 through inductive coupling, e.g. of the primary coil 152 of the external charger device 150 with the charging coil 112 of the IPG 110. The charger device 150 and IMD 110 may use a near field communication protocol, such as the Wireless Power Consortium (WPC) Qi wireless charging standard, Version 1.2.4 released in 2017 or other standard or proprietary protocol for communication during charging.

When charging the IMD 100, the housing of the charger device 150 may directly touch the patient's skin or in other examples, a charger holding device or the patient's clothing may lay between the charger device 150 and the patient's skin. The charger device 150 is moved across the patient's skin to lay above the tissue under which the IPG 110 is implanted. For an efficient inductive coupling, the primary coil 152 and the charging coil 112 should be in alignment with respect to one another, e.g. the primary coil 152 and the charging coil 112 should be within a predetermined distance and have a predetermined position relative to each other. Misalignment of the charger device 150 may introduce unexpected noise, trigger false detection of a presence of the IPG 110, and start false charging. The improper positioning may also lead to inefficient charging time, high charging power consumption or even generation of heat on undesired metal surfaces of the IMD.

In an embodiment, the positioning application 160, magnetic field sensor 114 and magnet 154 are used to determine an alignment of the charger device 150 relative to the IMD 100. During manufacture or configuration, the primary coil 152 is properly aligned with the charging coil 112 of the IMD 100 for charging. The magnetic field sensor 114 then outputs values proportional to the magnetic field strength detected along an X, Y, Z axes. Acceptable ranges of these values may be determined during such alignment.

In use, to recharge the IMD 100, the charger device 150 is moved along the patient's skin. The magnetic field sensor 114 detects the magnetic field generated by the magnet 154 and provides a value proportional to the magnetic field strength along an X, Y, Z axes. These values of the magnetic field are used to determine whether the primary coil 152 is properly aligned with the charging coil 112 in the IMD 100 for charging. When misaligned, the positioning application 160 generates one or more audible, visual, or tactile indicators to reposition the charger device 150. Since the positioning application 160 may determine a relative position of the charger device 150 and the IMD 110, it may also indicate directions for repositioning of the charger device 150 to improve alignment. In addition or alternatively, the position of the charger device 150 with respect to the IMD 100 (or with respect to a desired target area) may be determined and displayed in real time to further assist a user in positioning the charger device 150.

Figure 2:
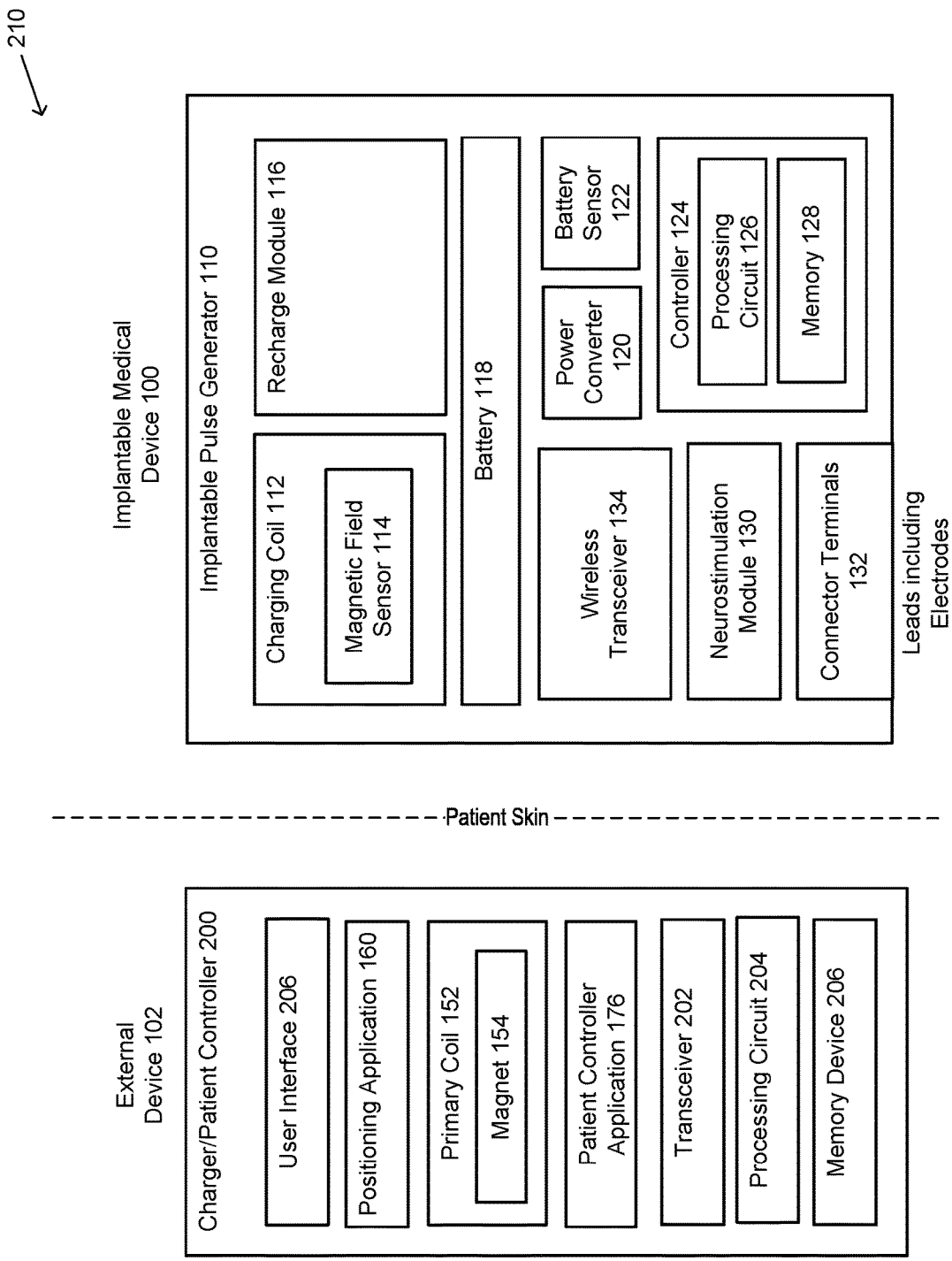
FIG. 2 is a schematic block diagram illustrating selected components of an IMD and another example of an external device according to some embodiments.

FIG. 2 is a schematic block diagram illustrating an embodiment of selected components of the IMD 100 and another embodiment of the external devices 102. In this system 210, the functions of the patient controller 170 and the charger device 150 are implemented in a single external device 102. The Charger/Patient Controller 200 may be a dedicated control device or a non-dedicated user device, such as a smart phone, smart tablet, smart watch, laptop, desktop, or any other external control device configured to control and charge the IPG 110. The Charger/Patient Controller 200 includes a transceiver 202 that is configured to communicate at least with the wireless transceiver 134 of the IPG 110 using one or more wireless protocols, e.g. such as those described herein.

The Charger/Patient Controller 200 further includes a processing circuit 204, memory device 206, the patient controller application 176, charger coil 152 with a magnet 154 and the positioning application 160. The memory device 206 stores programs, code, states, instructions and/or data that when executed or processed by the processing circuit 204 enables the charger/patient controller 200 to perform one or more functions described herein. The Charger/Patient Controller 200 may implement the Wireless Power Consortium (WPC) Qi wireless charging standard, Version 1.2.4 released in 2017 or other near field communication protocol, for communication during charging of the IMD 100. The user interface 206 includes one or more of a display, keyboard, touchscreen, touchpad, mouse or other such input or output devices.

Figure 3A:
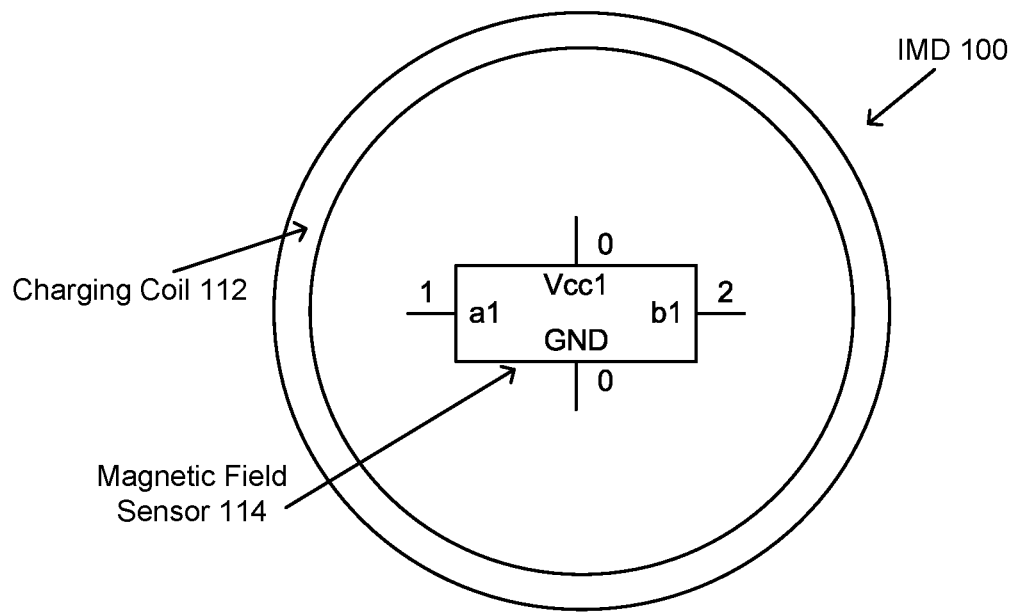
FIG. 3A is a schematic block diagram illustrating a charging coil and magnetic field sensor in an IMD according to some embodiments.

FIG. 3A is a schematic block diagram illustrating an embodiment of the charging coil 112 and magnetic field sensor 114 in the IMD 100. Though the charging coil 112 is illustrated as circular, the charging coil 112 may be formed in alternative shapes. In an embodiment, the magnetic field sensor 114 is positioned in proximity to the charging coil 112 of the IMD 100, e.g. within 4 cm of the charging coil 112 or within a circumference of the charging coil 112. In this example, the magnetic field sensor 114 is positioned at approximately a center of the wire windings of the charging coil 112 in a same plane, e.g. on a same PCB. In other examples, the charging coil 112 may be wound around a PCB and the magnetic field sensor 114 may be implemented on the PCB or otherwise in proximity to the charging coil 112.

In an embodiment, the magnetic field sensor 114 is configured to detect a static magnetic field and to output a value proportional to the static magnetic field along three dimensions, such as along each of the X, Y, and Z axes. The magnetic field sensors 114 may utilize three Hall Effect sensors, one along each of the X, Y and Z axes in the integrated circuit. The Hall Effect sensors measure a potential difference created by charges that separate to opposite sides of a conductor in the presence of the magnetic field. For example, the magnetic field sensor 114 may be implemented using the Melexis® MLX90393—Triaxis® micropower magnetometer. Other magnetic field sensors may be implemented such as the Anisotropic Magneto-Resistive (AMR)® sensors or such as the Infineon® 3D sensor XENSIV™ that detects the strength of a magnetic field in three dimensions, i.e. X, Y, and Z axes. Though Cartesian coordinates are described herein, the magnetic field strength may be expressed along other three-dimensional coordinates, such as cylindrical coordinates or spherical coordinates.

Figure 3B:
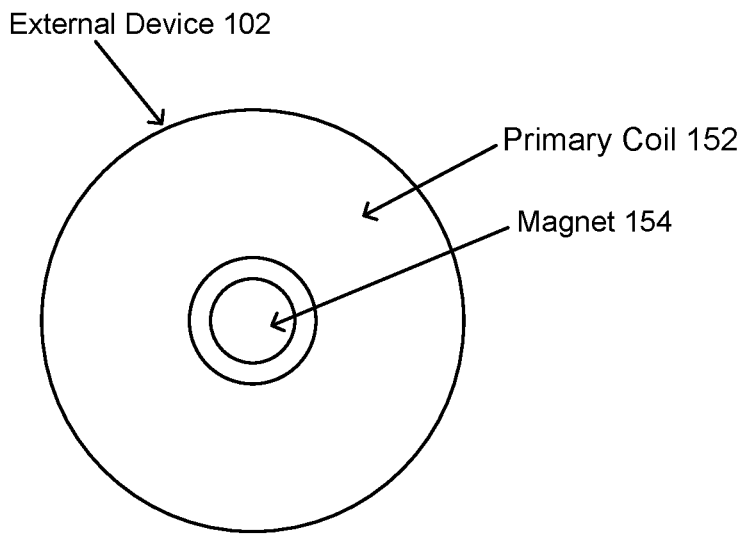
FIG. 3B is a schematic block diagram illustrating an embodiment of a primary coil and magnet in an external device according to some embodiments.

FIG. 3B is a schematic block diagram illustrating an embodiment of a primary coil 152 and magnet 154 in an external device 102. Though the primary coil 152 is illustrated as circular, the primary coil 152 may be formed in alternative shapes. In an embodiment, the magnet 154 has a predetermined polarization and a static magnetic field. The magnet 154 may be axially magnetized or diametrically magnetized. The magnet 154 is positioned in proximity to the primary coil 152 of the external device 102, e.g. within 4 cm of the primary coil 152, or within a circumference of the primary coil 152. In FIG. 3B, the magnetic 154 is positioned at approximately a center of the wire windings of the primary coil 152 in a same plane, e.g. on a same PCB. In other examples, the primary coil 152 may be wound around a PCB and the magnet 154 may be implemented on the PCB or otherwise in proximity to the primary coil.

The magnet 154 generates a static or constant magnetic field which does not change in intensity or direction over time with respect to a fixed point, such as the primary coil 152. Since the magnet 154 is polarized (North-South or East-West), the magnetic field sensor 114 may also detect an orientation of the charger device 150 as well as the intensity of the magnetic field. For example, when a the magnet 154 is North-South polarized, the North pole of the magnet 154 may face the charger pad side of the charger device 150. The magnetic field strength sensor 114 will detect a magnetic field having a first polarization when the charger pad side nears the magnetic field sensor 114. If an opposing side of the charger device 150 nears the magnetic field sensor 114, then the magnetic field sensor 114 will detect a magnetic field having a second polarization. This change in polarization is detected by the Hall effect sensors in the magnetic field sensor 114 as a positive or negative current. Thus, an orientation of the charger device 150 (such as front facing or back facing) with respect to the magnetic field sensor 114 may be detected.

In this embodiment, the magnetic field sensor 114 is implemented in the IMD 100 while the magnet 154 is implemented in the external device 102. This arrangement is preferable to allow MRI scans of a patient with the IMD 100. However, when MRI scans of a full body of the patient are not a priority, the magnetic field sensor 114 may be implemented in the external device 102 while the magnet is implemented in the IMD 100. Similar protocols as described herein may then be implemented to determine an alignment of the external charger device 102.

Figure 4A:
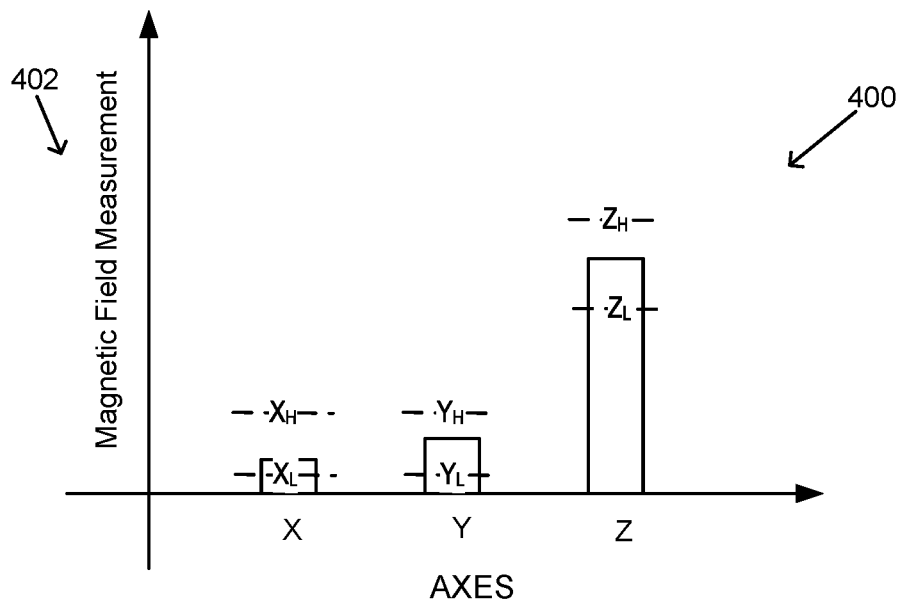
FIG. 4A is a graphical representation of magnetic field measurements of a static magnet field determined using the magnetic field sensor according to some embodiments.

FIG. 4A is a graphical representation 400 of magnetic field measurements 402 for a static magnet field determined using the magnetic field sensor 114 in an IMD 100. In an embodiment, a static magnetic field measurement 402 is generated using the magnetic field sensor 114 for each of the X, Y and Z axes. Static magnetic fields are constant fields and do not change in intensity or direction with respect to a fixed point over time, e.g. in contrast to low or high frequency alternating magnetic fields. Hence, the static magnetic field has a frequency of 0 Hz. The strength of a static magnetic flux density is expressed in tesla (T) or in some countries in gauss (G). The magnetic field measurement 402 thus may be a value proportional to the static magnetic flux density B, which is measured in tesla (in SI base units: kilogram per second$^2$ per ampere). In another embodiment, the magnetic field measurement 402 may be a value proportional to magnetic field strength, H, which is measured in the SI base units of ampere per meter (A/m). Other measurements of the magnetic field may additionally or alternatively be used as the magnetic field measurement 402 and be obtained by the magnetic field sensor 114 along three dimensions. The direction or polarization of the static magnetic field may also be determined along each of the axes.

The magnetic field measurements 402 are used to determine the position or alignment of the primary coil 152 with respect to the charging coil 112. In one embodiment, a range of static magnetic field measurements 402 for each of the X, Y and Z axes is predetermined such that the charger coil 112 and primary coil 152 are properly aligned when the magnetic field measurements 402 are within these ranges ($X_L$-$X_H$, $Y_L$-$Y_H$, $Z_L$-$Z_H$). These predetermined thresholds may be determined during configuration, testing and/or manufacture of the charger device 150 and IMD 100. For example, during manufacture, for a certain type and size of magnet 154 and certain model of the magnetic field sensor 114, the charger coil 112 in the IMD 100 and primary coil 152 in the charger device 154 are aligned for efficient inductive coupling. A range of static magnetic field measurements 402 for each of the X, Y and Z axes is obtained over a range of relative positions of alignment and over a range of temperatures. The range of temperatures may be the temperature measured at the magnet 154 or at the magnetic field sensor 114 or both. The range of magnetic field measurements 402 for each of the three XYZ axes is obtained for the range of relative positions of the charger device 150 while maintaining alignment for efficient inductive coupling. This range of magnetic field measurements 402 is used to determine the predetermined thresholds for alignment in each of the X, Y, and Z axes and are configured or programmed into one or more of the charger device 150, the IMD 100 or the patient controller 170.

The efficient inductive coupling may be defined by one or more of: absence of unwanted eddy currents in the IMD 100, noise within a predetermined S/N ratio, current generated in the charging coil 112 is above a predetermined threshold or the power transfer efficiency is above a predetermined threshold. For example, the power transfer efficiency can be quantified as the coupling coefficient "k" between the primary coil 152 in the charger device 150 and the charging coil 112 in the IMD. The coupling coefficient k is defined as the ratio of transformer open-circuit voltage ratio to the ratio that would be obtained if all the flux coupled from one coil to the other. The coupling coefficient k ranges between 0 and 1 and measures the extent to which power expended at the primary coil 152 is received at the charging coil 112. Higher coupling results in faster charging of the IMD 100 with lower expenditure of power in the charger device 150. Poor coupling results in a high power drain in the charger device 150 to adequately charge the IMD 100. The coupling coefficient is a function of the geometry of the system and depends on the positional relationship between the two coils. The Wireless Power Consortium advises that a coupling coefficient k in the range of 0.3 to 0.6 is typical depending on the X-Y alignment and the distance Z between the inductive coils (due to the depth of the IMD in the tissue). Thus, an efficient inductive coupling may be defined as k≥0.3.

Figure 4B:
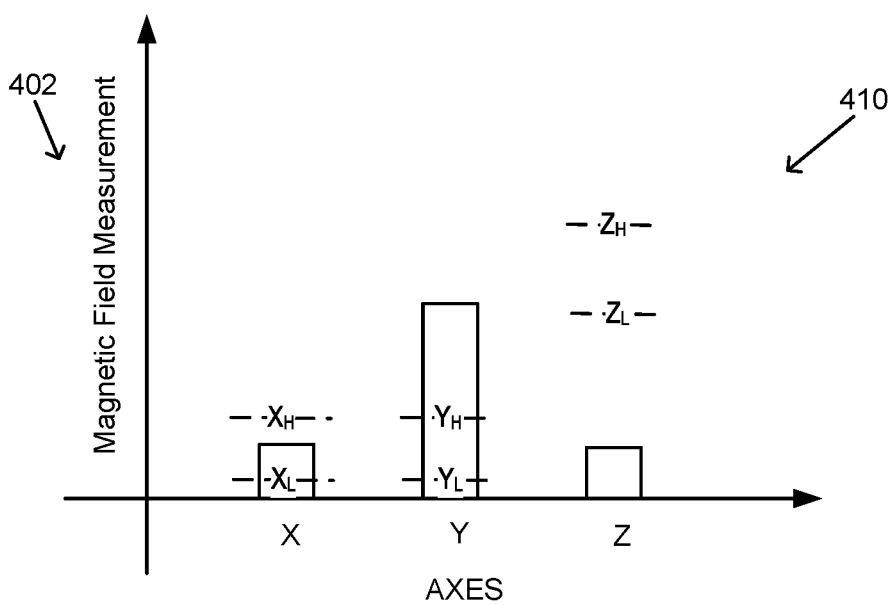
FIG. 4B is another graphical representation of the static magnetic field measurements determined using the magnetic field sensor according to some embodiments.

FIG. 4B is a graphical representation 410 of another measurement of the static magnetic field measurements 402. In this example, the charger device 150 is not properly aligned with the IMD 100. For example, though the detected magnetic field measurement along the X axis is within the predetermined thresholds ($X_L$-$X_H$), the determined static magnetic field measurements 402 for each of the Y and Z axes are not within the predetermined thresholds ($Y_L$-$Y_H$, $Z_L$-$Z_H$). Thus, it would be determined that the charger device 150 is not aligned for efficient inductive coupling.

The zero or near-zero frequency (e.g., DC level) of the magnetic field strength is measured to determine the static magnetic field generated by the magnet 154. Thus, the static magnetic field strength may be isolated from the magnetic field generated by the primary coil 152. For example, the static magnetic field generated by the magnet 154 may be determined during charging, e.g. during generation of the alternating or modulating magnetic field generated by the primary coil 152 or charging coil 112, by isolating the DC or near-zero frequency magnetic field. The position or alignment of the charging device 150 may thus be determined even during charging or activation of the primary coil 152.

Figure 5A:
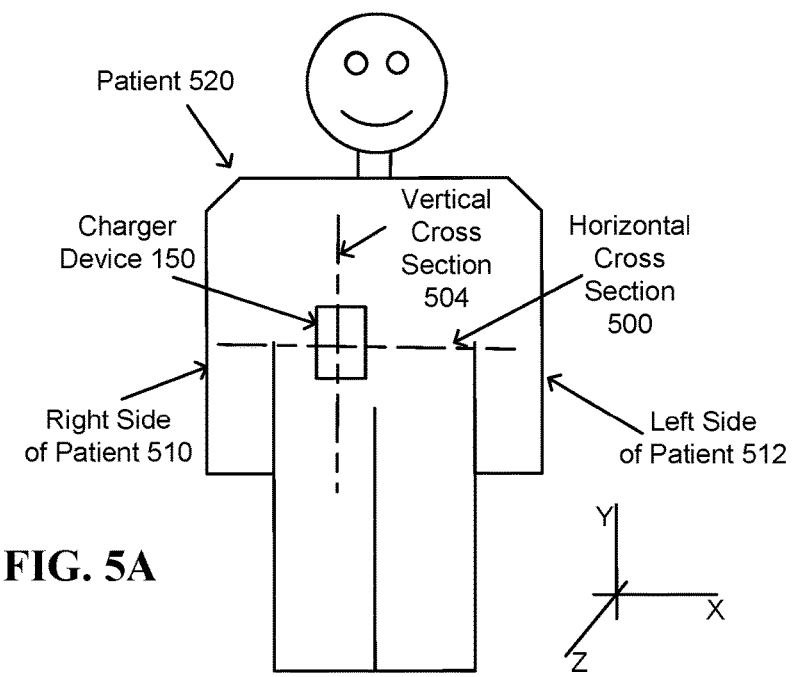
FIGS. 5A, 5B, 5C, 5D, 5E and 5F are schematic block diagrams illustrating alignment of a charger device and IMD according to some embodiments.

FIGS. 5A-5F are schematic block diagrams illustrating alignment of the charger device 150 and IMD 100 for efficient inductive coupling. Efficient inductive coupling is affected by the alignment or positional relationship of the charger device 150 and IMD 100. FIG. 5A illustrates the charger device 150 positioned over the skin of a patient 520. For these examples in FIGS. 5B-5F, the charger device 150 includes a horizontal cross section 500 and a vertical cross section 504. The right side 510 and left side 512 of the patient 520 are also indicated.

Figure 5B:
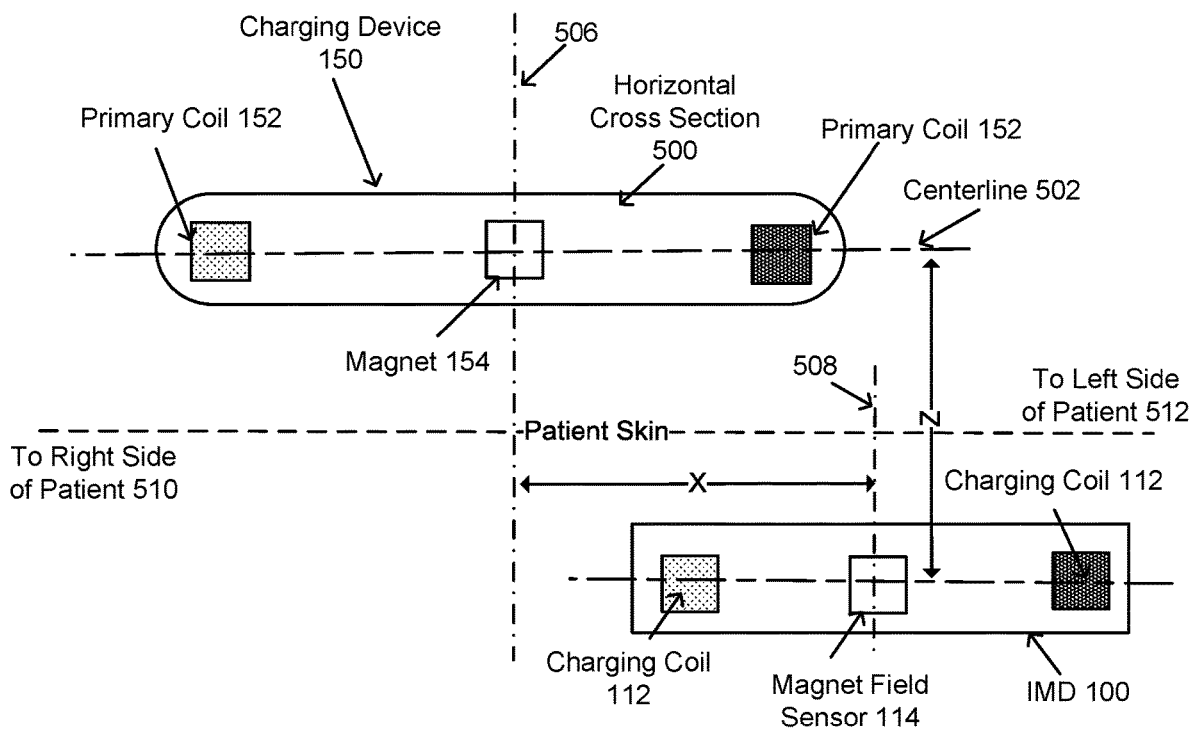
Figure 5C:
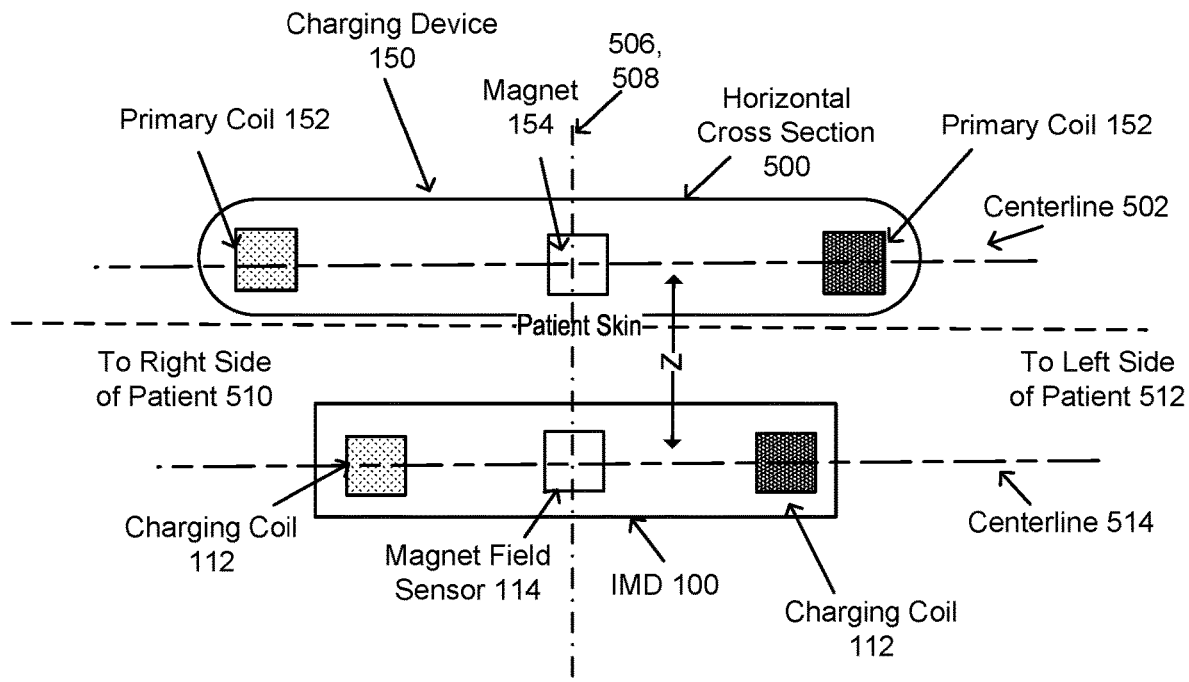

FIG. 5B illustrates the horizontal cross section 500 of the charger device 150 and a cross section of the IMD 100. The horizontal cross section 500 of the charger device shows a centerline 502 of a center plane of the wire windings of the primary coil 152. In this embodiment, the magnet 154 of the charger device 150 is positioned on the centerline 502 and on the central axis 506 of the wire windings of the primary coil 152. Moreover, in this example, the magnetic field sensor 114 of the IMD 100 is positioned on a central axis 508 of the wire windings of the charging coil 112. For efficient inductive coupling (higher values of k), it is preferred that the coils are axially aligned, e.g. the axes 506 and 508 around which the primary coil 152 and the charging coil 112 are wound respectively are collinear and parallel to decrease the distance X.

In an embodiment, the magnetic field measurements 402 from the magnetic field sensor 114 are used to determine the relative position or distance of the charger device 150 relative to the IMD 100 along the X axis and indications are provided to move the charger device 150 in a direction to decrease or lessen the distance X between the axes 506, 508 of the coils. In this example, the directions would indicate to move the charger device 150 towards the left side of the patient. For example, in FIG. 5C, the charger device 150 has been moved more towards the left side of the patient from that shown in FIG. 5B such that axes 506 and 508 around which the primary coil 152 and the charging coil 112 are wound are now collinear and parallel.

In addition, for efficient inductive coupling (higher values of k), it is preferred that the distance Z is minimized. The distance Z indicates the depth between the charger device 150 and the IMD 100 along the Z axis perpendicular to the centerline 502 of the center plane of the wire windings of the primary coil 152 and/or charging coil 112. This distance Z may not be completely eliminated since the charger device 150 is generally placed on the patient's skin, and the IMD 100 has been implanted at a particular depth within the tissue of the patient. However, the distance Z may be decreased by removing clothing or a holder for the charger device 150. For example, the distance Z has been decreased in FIG. 5C from that shown in FIG. 5B by positioning the charger device 150 closer to the patient's skin. Thus, in an embodiment, the magnetic field measurements 402 from the magnetic field sensor 114 may be used to determine the position of the charger device 150 relative to the IMD 100 along the Z axis and provide indications to move the charger device 150 in a direction to decrease the distance Z. For example, the indications may include to move the charger device 150 in closer proximity to the skin of the patient 520 such that a relative distance from a center of the primary coil 152 in the charger device 150 and a center of the charging coil 112 in the IMD 100 is decreased.

Figure 5D:
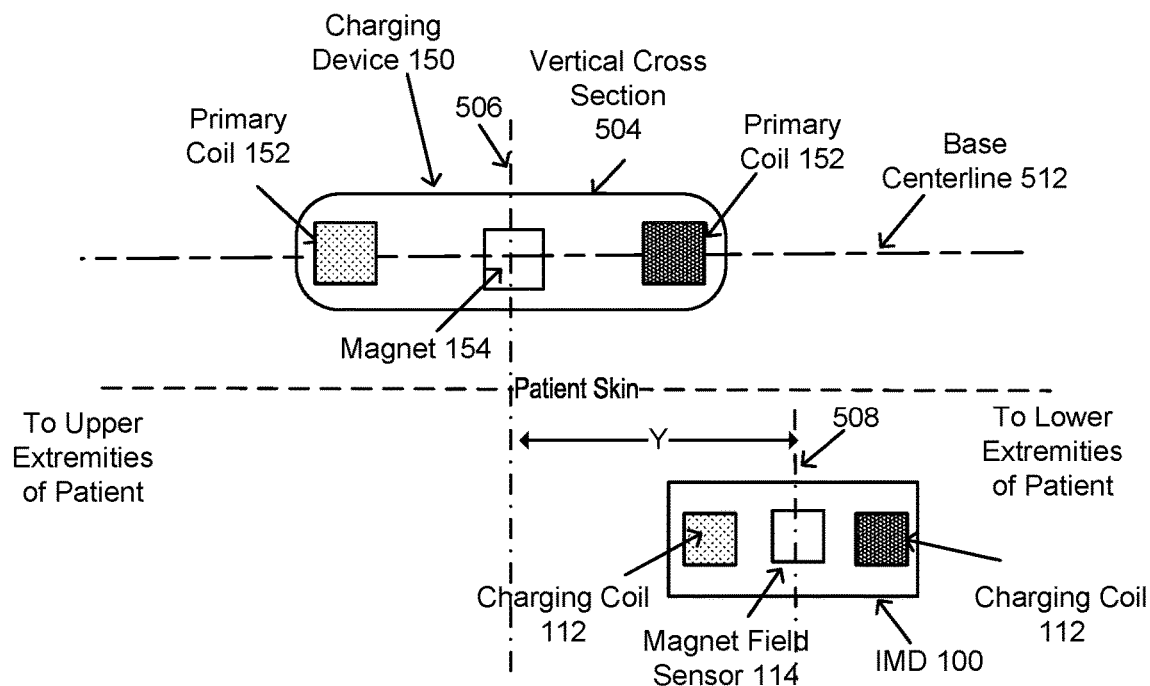

FIG. 5D illustrates the vertical cross section 504 of the charger device 150. In this embodiment, the magnet 154 of the charger device 150 is positioned on the base centerline 512 and on the central axis 506 of the wire windings of the primary coil 152. Moreover, in this example, the magnetic field sensor 114 of the IMD 100 is positioned on the central axis 508 of the wire windings of the charging coil 112. For efficient inductive coupling (higher values of k), it is preferred that the axes 506 and 508 are axially aligned, e.g. collinear and parallel to minimize the distance Y. Similarly as the distance X needs to be decreased in FIG. 5B, the distance Y also needs to be decreased, such that the axes 506 and 508 are collinear in both the X and Y directions. In an embodiment, the magnetic field measurements 402 from the magnetic field sensor 114 are used to determine a relative position or distance of the charger device 150 relative to the IMD 100 along the Y axis and indications are provided to move the charger device 150 in a direction to decrease or lessen the distance Y between the axis 506 and the axis 508. In this example, indications would be generated to move the charger device 150 in a direction towards the lower extremities (or away from the upper extremities) of the patient 520.

Figure 5E:
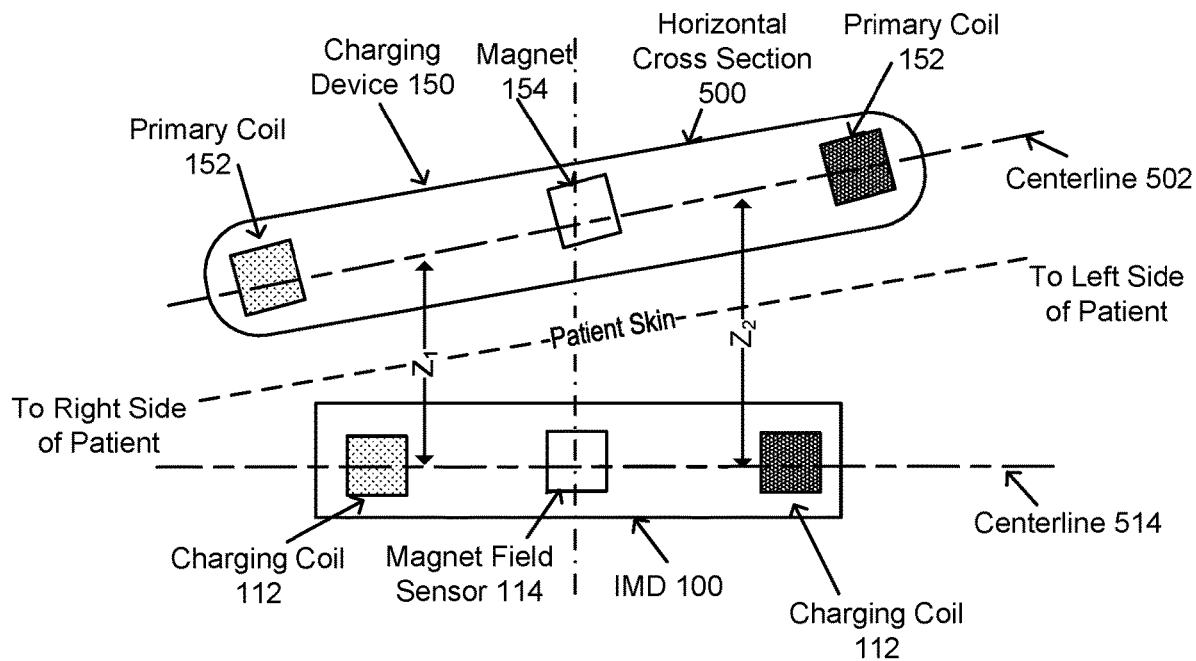

FIG. 5E illustrates another example of the horizontal cross section 500 of the charger device 150 in which the charger device 150 is tilted or angled with respect to the IMD 100. For example, the centerline 506 of the charging coil 112 in the IMD 110 is at an angle with respect to the patient's skin and/or the IMD 100. For efficient inductive coupling (higher values of k), the primary coil 152 of the charger device 150 and the charging coil 112 of the IMD 100 should be relatively parallel, e.g. at less than a 20 degree angle. For example, the plane perpendicular to the axis 506 and through the primary coil 152 is preferably parallel to the plane perpendicular to the axis 508 and through the charging coil 112. In this example, the primary coil 152 is tilted or angled along the Y axis relative to the charging coil 112 such that a first end of the charging device has a lower Z distance to the IMD 100 than a second end of the charging device, e.g. $Z_1 < Z_2$.

Figure 5F:
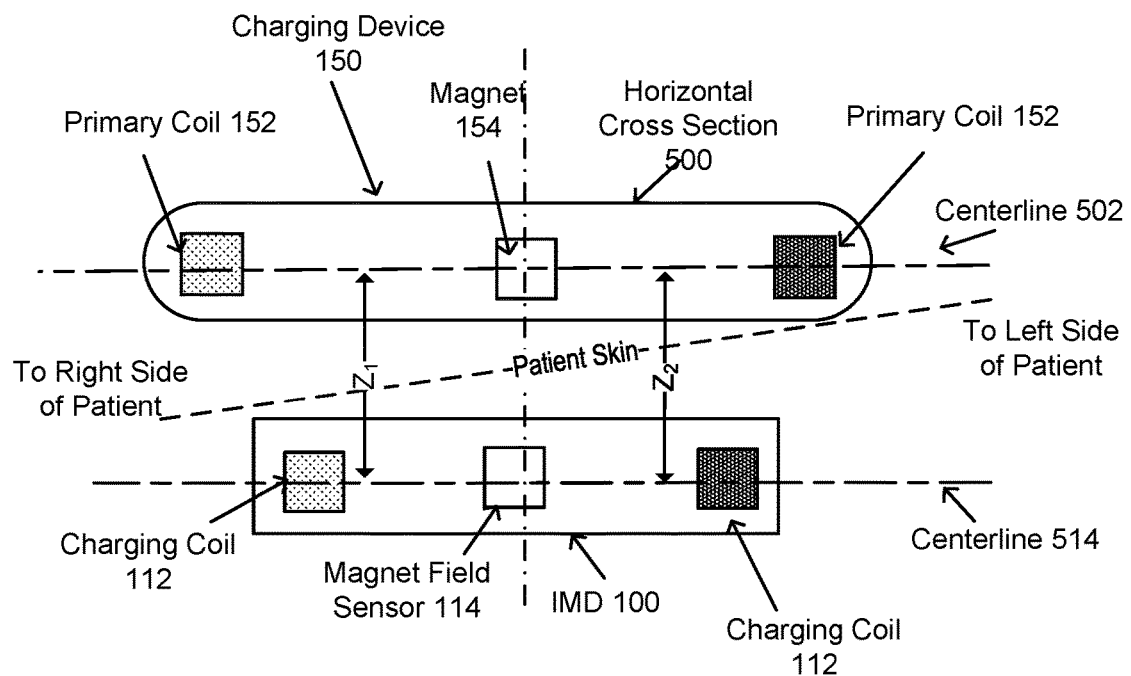

As such, in an embodiment, the magnetic field measurements 402 from the magnetic field sensor 114 may be used to determine that the charger device 150 is tilted or angled with respect to the IMD 100. Directions may be generated to rotate or tilt a portion of the charger device 150 (e.g., top, bottom, top left corner, left side, right side, etc.) towards the patient's skin or away from the patient's skin such that the primary coil 152 and the charging coil 112 are in a more parallel position. For example, as shown in FIG. 5F, the right side of the charger device 150 has been rotated away from the patient's skin such that the centerline 502 of the primary coil 152 in the charger device 150 is in a more parallel position to the centerline 514 of the charging coil 112 in the IMD 100 and so that $Z_1$ is more equidistant to $Z_2$.

The present embodiments are thus able to detect a relative position and distance of the charger device 150 with respect to the IMD 100 in three dimensions. For example, a relative distance of the external device to the IMD is determined in the X direction, Y direction and Z direction using the static magnetic field measurements 402. An angle or tilt of the charger device 150 relative to the IMD 100 may also be determined. Thus, directions may be determined to improve alignment, such as to move the charger device 150 to the right or left or upwards or downwards, along the skin, may be provided to a user as well as directions to tilt or angle the charger device 150. In addition, an orientation of the charger device 150 (back or front facing the patient skin) may be determined and instructions provided to change the orientation of the charger device 150.

Figure 6A:
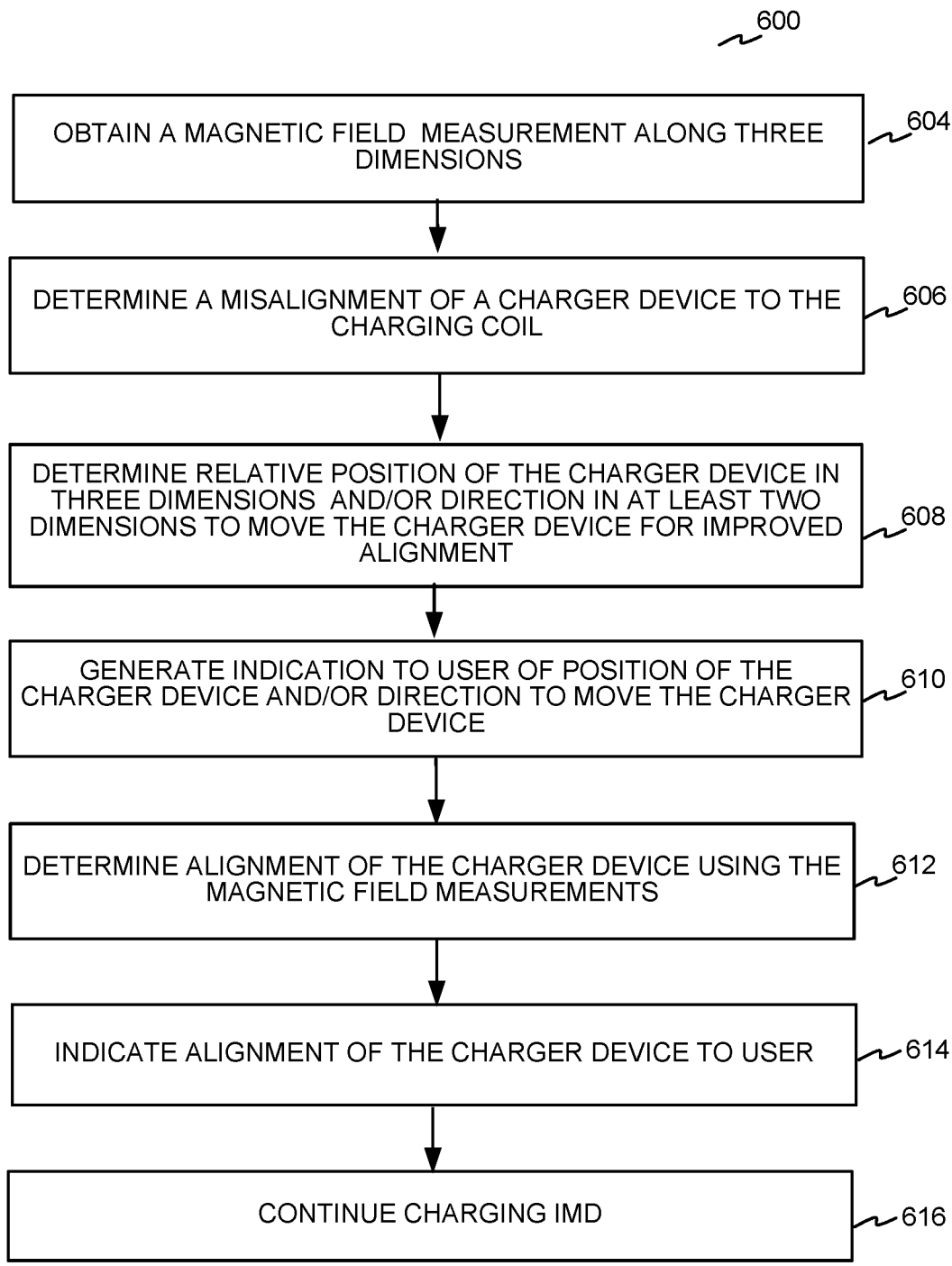
FIG. 6A is flow diagram illustrating a method for alignment of an external charger device according to some embodiments.

FIG. 6A is flow diagram illustrating a method 600 for alignment of an external charger device 150 according to some embodiments. When the charger device 150 approaches a vicinity of the IMD 100, the IMD 100 determines that a charger device 150 is within a predetermined range of the IMD 100. The magnetic field sensor 114 may detect a magnetic field strength of the magnet 154 that is above a predetermined threshold indicating that a primary coil 152 of the charger device 150 is within a certain range and is able to initiate charging. In another embodiment, the charging coil 112 of the IMD 100 may detect a flow of current, voltage level or an impedance above a predetermined threshold indicating that a primary coil 152 of the charger device 150 is within a predetermined range and is able to initiate charging. In another embodiment, other proximity sensors may be implemented that are configured to detect the charger device 150 is within a predetermined range to the IMD 100 to initiate charging.

When the charger device 150 is within such predetermined range, the IMD 100 initiates the magnetic field sensor 114 to output measurements of the detected magnetic field along each of three dimensions, e.g. X, Y, and Z axes at 604. The static magnetic field sensor 114 continues to periodically output the magnetic field measurements, e.g. at one or more times per second, until indicated by the IMD 100 to halt. The magnetic field measurements 402 may be determined and processed by the controller 124 of the IMD 100. In another example, the controller 124 may generate one or more messages including the magnetic field measurements 402 in each of three dimensions. The magnetic field measurements 402 may then be transmitted to the charger device 150 by the IMD 100 for processing. In another case, the magnetic field measurements 402 may be transmitted to a patient controller 170 or other user device for processing.

The magnetic field measurements 402 are processed to determine a misalignment of the charger device 150 to the IMD 100 at 606. For example, the magnetic field measurement 402 for each of the X, Y, and Z dimensions may be compared to predetermined thresholds that were determined during an efficient inductive coupling, e.g. as shown in FIG. 4A. In use, the magnetic field measurement 402 for each of the XYZ axes is compared to the predetermined thresholds for the measured temperature, e.g. the temperature measured at either the magnet 154 or magnetic field sensor 114 or both. For example, the magnetic field measurement 402 along the X axis is compared to a range of $X_L$-$X_H$, the magnetic field measurement 402 along the Y axis is compared to a range of $Y_L$-$Y_H$ and the magnetic field measurement 402 along the Z axis is compared to a range of $Z_L$-$Z_H$. When the magnetic field measurement 402 for any of the X, Y and Z axes is not within the predetermined thresholds, it is determined that the charger coil 112 and primary coil 152 are misaligned at 606.

In another embodiment, the magnetic field measurement 402 for each of the X, Y, and Z axes are used to determine a position of the charger device 150 relative to the IMD 100, e.g. as shown in FIGS. 5A-F. When the position of the charger device 150 is within certain linear distance thresholds from the IMD 100 in the X, Y and Z axes or other three dimensional coordinates, the charger device 150 is determined to be aligned with the IMD 100. For example, a linear distance threshold may include that the distance in the X direction between the axis 506 of the primary coil and the axis 508 of the charging coil is between 0-4 mm. Similarly, another linear distance threshold may include that the distance in the Y direction between the axis 506 of the primary coil and the axis 508 of the charging coil is between 0-4 mm. Alternatively, a linear distance threshold may include that the total distance in the X-Y plane between the axis 506 of the primary coil and the axis 508 of the charging coil is between 0-6 mm. In addition, another linear distance threshold may include that the distance in the Z direction between the primary coil 152 and the charging coil 112 is between 2-50 mm. Moreover, alignment may also require that the horizontal centerline 502 of the primary coil 152 and the horizontal centerline 514 of the charging coil 112 are in a more parallel position, e.g. at less than a 20 degree angle or another threshold. These distances and angles are exemplary only and other linear distance thresholds or angles may be determined during manufacture or configuration. Alignment may also require a correct orientation of the charger device 150, e.g. front facing or charger pad towards the patient's skin.

When misaligned, the magnetic field measurements 402 are used to determine a relative position of the charger device 150 with respect to the charging coil 112 and/or a direction to move the charger device 150 for improved alignment at 608. The relative position of the charger device 150 and/or the direction to move the charger device 150 is generated in two or three dimensions at 610. Thus, the magnetic field sensor 114 and magnet 154 provide a means to determine the position of the primary coil 152 relative to the charging coil 112 in three dimensions. A user may thus be informed to move or rotate the charger device 150 in one or more of the X, Y or Z directions. For example, an indication may be generated to move the charger device 150 along the Z axis (e.g. closer or further from the patient's skin). In another example, an indication may be generated to move the charger device 150 in an X direction (e.g., to the left or right side of the patient) or in a Y direction (e.g., upwards towards the head or downwards towards the lower extremities) or in both an X and Y direction. In another example, an indication may be to rotate or tilt a portion of the charger device 150 to change an angle or tilt of the charger device 150 to improve alignment.

The magnetic field sensor 114 continues to output measurements of the detected magnetic field. The position of the charger device 150 and/or indications to move the charger device 150 are continued to be generated and provided to a user until an alignment of the charger device 150 is determined at 612. Alignment of the charger device 150 occurs when the charger device 150 is within a relative position to the IMD 100 for efficient inductive coupling.

The alignment of the charger device 150 is indicated to the user at 614. The user should then halt further movement of the charger device 150 and hold or otherwise secure the charger device 150 in the aligned position. The charger device 150 may then continue or begin charging the IMD 100 at 616. If the charger device 150 becomes misaligned during charging, an alert may be generated. The position of the charger device 150 and/or indications to move the charger device 150 may then again be provided until an alignment of the charger device 150 is again determined. The charger device 150 may halt charging during the misalignment and resume charging when the charger device 150 is again aligned with the IMD 100. Or the charger device 150 may continue to charge the IMD 100 during the alignment process.

Figure 6B:
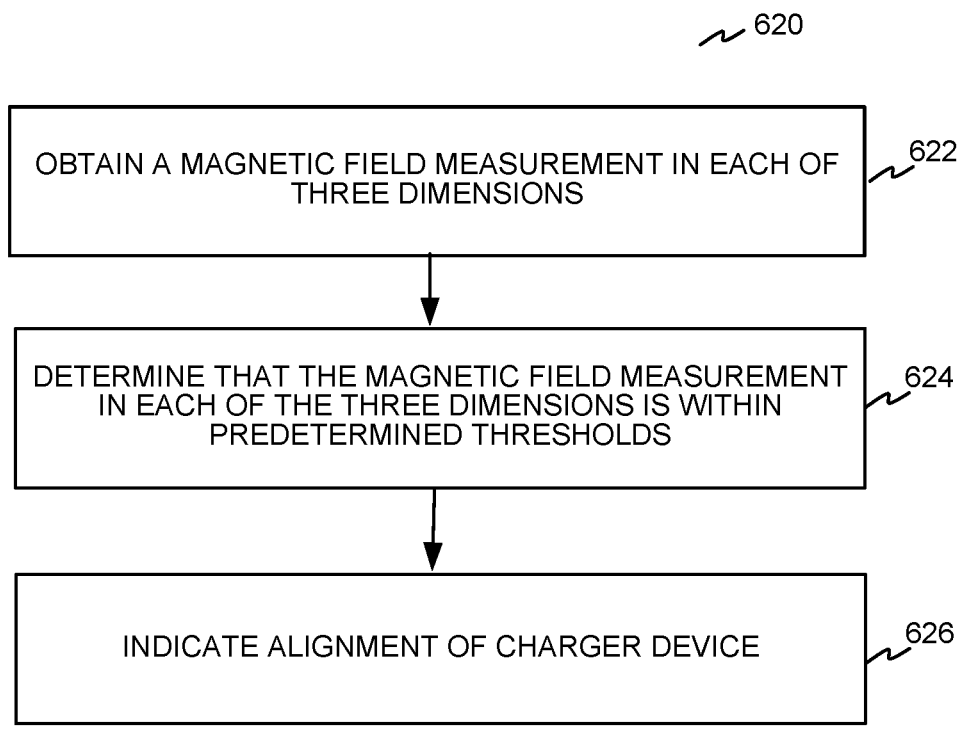
FIG. 6B is flow diagram illustrating another method for alignment of an external charger device according to some embodiments.

FIG. 6B is a flow diagram illustrating a method 620 for alignment of the external charger device 150 according to some embodiments. Magnetic field measurements 402 are obtained in each of three dimensions, e.g. along each of the X, Y, and Z axes, at 622. The magnetic field measurement 402 for each of the X, Y, and Z axes is compared to predetermined thresholds. For example, the magnetic field measurement 402 along the X axes is compared to a range of $X_L$-$X_H$, the magnetic field measurement 402 along the Y axes is compared to a range of $Y_L$-$Y_H$ and the magnetic field measurement 402 along the Z axes is compared to a range of $Z_L$-$Z_H$. In this embodiment of FIG. 6B, the magnetic field measurement 402 for each of the X, Y, and Z axes is within the predetermined thresholds at 624. As such, it is determined that the charger device 150 and IMD 100 are properly aligned, e.g. within a relative position in the X, Y and Z dimensions for efficient inductive coupling. This alignment of the charger device 150 is then indicated to a user by either an audible, visible, or tactile means at 626.

Figure 6C:
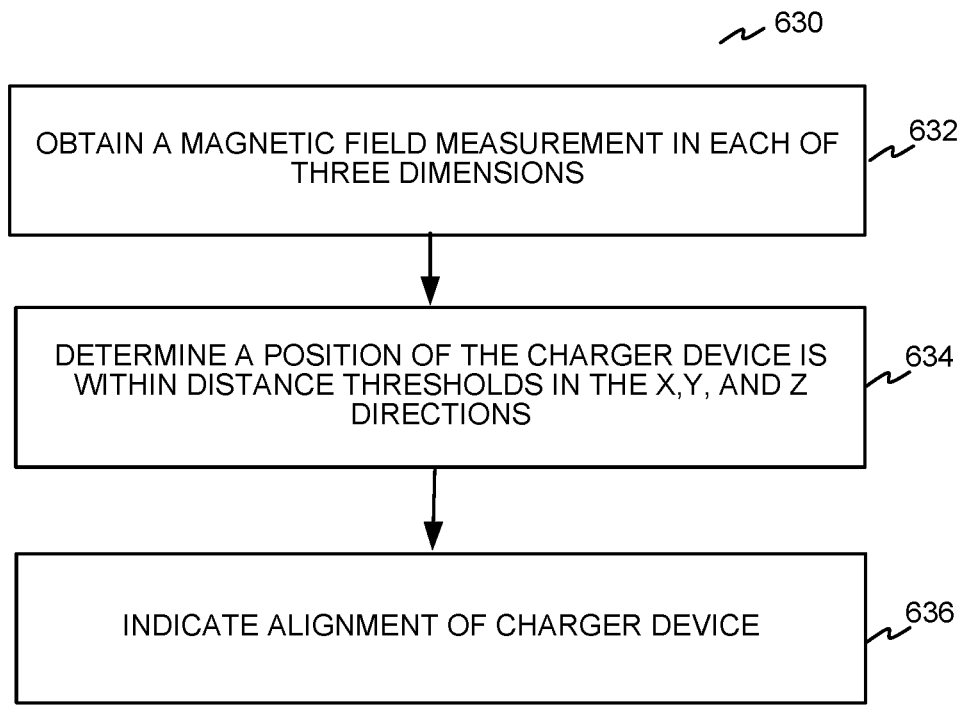
FIG. 6C is flow diagram illustrating another method of determining an alignment of the external charger device according to some embodiments.

FIG. 6C is flow diagram illustrating another method 630 of determining an alignment of the external charger device 150 according to some embodiments. Magnetic field measurements 402 are obtained in each of three dimensions, e.g. along each of the X, Y, and Z axes, at 632. The magnetic field measurement 402 are processed to determine a relative position of the primary coil 152/charger device 150 to the charging coil 112/IMD 100. If the relative position is at least within predetermined linear distance thresholds, e.g. in the X, Y and Z directions, it is determined that the charger device 150 and IMD 100 are properly aligned at 634. This alignment of the charger device 150 is then indicated to a user by either an audible, visible, or tactile means at 636

Additional parameters may also be considered in the determination of alignment. For example, alignment may also mean that the centerline 502 or plane through the wire windings of the primary coil 152 is relatively parallel to the centerline 514 or plane through the wire windings of the charging coil 112 in the IMD 100. For example, the absolute value of the difference $Z_1$-$Z_2$ in FIG. 5F is less than a predetermined threshold or an angle between the two planes is less than 20 percent. In addition, the orientation of the charger device 150 must have the charging pad towards the patient skin. Using one or more of these parameters, it is determined that the charger device 150 and IMD 100 are properly aligned for efficient inductive coupling. Efficient inductive coupling may be defined as a relatively higher k value, such as k≥0.3.

Figure 7A:
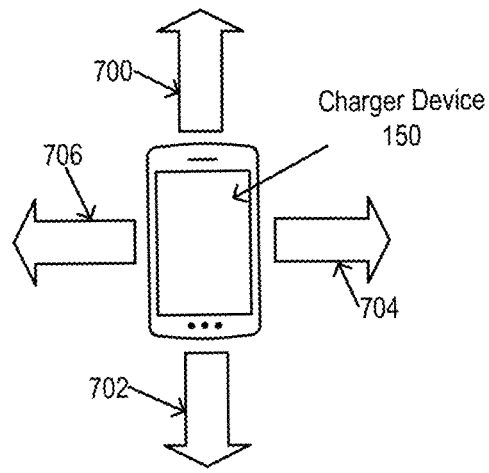
FIGS. 7A, 7B, 7C and 7D are graphical representations of embodiments of graphical user interfaces (GUIs) that are generated to provide indications of a direction to move an external charger device according to some embodiments.

FIGS. 7A, 7B, 7C and 7D are graphical representations of embodiments of graphical user interfaces (GUIs) that are generated to provide indications of a direction to move the charger device 150. For example, when a misalignment of the charger device 150 and the IMD 100 is determined, one or more GUIs may be generated to indicate a direction to move the charger device 150. FIG. 7A illustrates a first GUI generated on a display that includes a representation of the charger device 150 and arrows that indicate to move the charger device 150. For example, the left arrow 706 and right arrow 704 may indicate to move the charger device 150 to the left side or right side of the patient respectively The up arrow 700 or down arrows 702 may indicate to move the charger device 150 towards the head/upper extremities or towards the lower extremities, respectively.

Figure 7B:
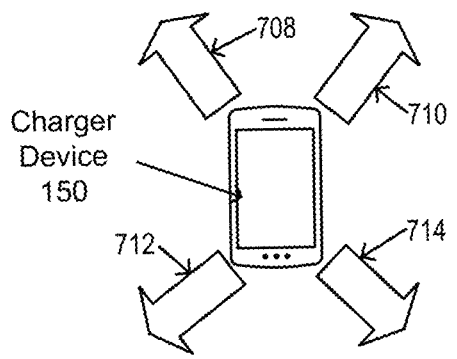
Figure 7C:
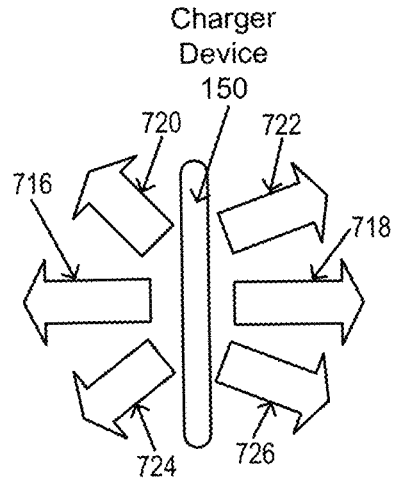

FIG. 7B illustrates a second GUI generated on a display that includes a representation of the charger device 150 and arrows that indicate to move the charger device 150 in a diagonal direction along the patient's skin (the upper left diagonal arrow 708, right upper diagonal arrow 710, lower left diagonal arrow 712 or lower right diagonal arrow 714). FIG. 7C illustrates a third GUI generated on a display that includes a representation of the charger device 150 and arrows that indicate to move the charger device 150 closer to the patient's skin or further from the patient's skin (left arrow 716 or right arrow 718) or to tilt the top portion or bottom portion of charger device closer or further from the patient's skin (the upper left diagonal arrow 720, right upper diagonal arrow 722, lower left diagonal arrow 724 or lower right diagonal arrow 726).

Figure 7D:
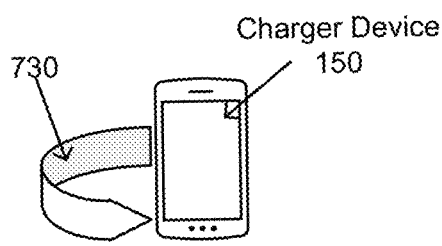

FIG. 7D illustrates a GUI on a display showing a charger device 150 and an arrow 730 that may be used to indicate to rotate or flip the charger device 150 from a first external side to a second external side. The arrow may thus indicate to rotate the charger device 150 such that a different external side is adjacent to the patient skin. For example, the different external side may include the charging pad and should be adjacent to the patient skin.

Though the indications to move the charger device 150 are visual in these figures, audible indications or tactile indications may be provided in addition to or alternatively to these visual indications. The GUI or other indications may be generated by the charger device 150 or the patient controller 170 or another user device.

Figure 8A:
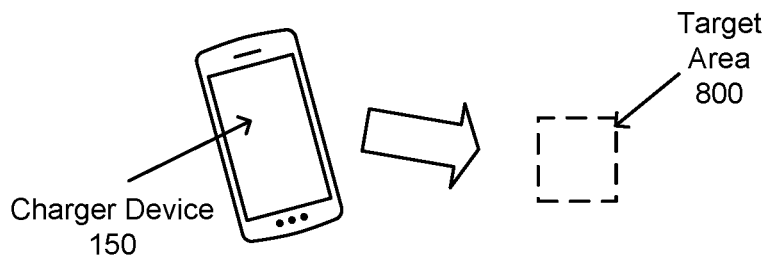
FIGS. 8A, 8B, 8C, 8D and 8E are graphical representations of additional embodiments of graphical user interfaces (GUIs) that provide indications of a position of a charger device with respect to a target area according to some embodiments.

FIGS. 8A-E are graphical representations of additional embodiments of graphical user interfaces (GUIs) that provide indications of a position of the charger device 150 with respect to a target area 800. For example, when a misalignment of the charger device 150 and the IMD 100 is determined, one or more GUIs may be generated to indicate a position of the charger device 150 with respect to the IMD 100. FIG. 8A illustrates a GUI generated on a display that includes a representation of the charger device 150 and a target area 800. The target area 800 may represent an aligned position for the charger device 150. The position of the charger device 150 is determined from the magnetic field measurements 402 and displayed on the GUI in relation to the target area 800.

Figure 8B:
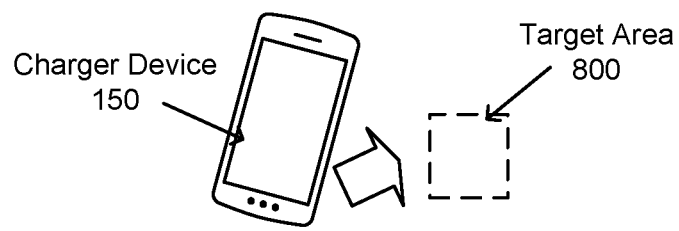
Figure 8C:
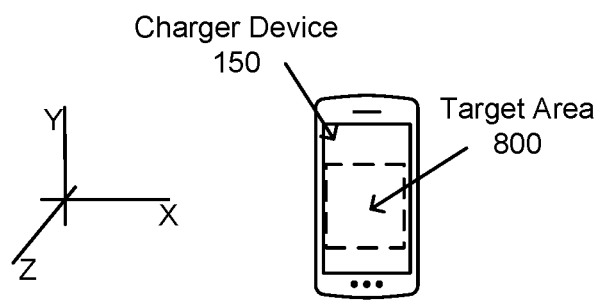

FIG. 8B illustrates a GUI generated on the display showing the charger device 150 being moved closer to the target area 800, e.g. in the X-Y plane. As the charger device is moved, the position of the charger device 150 is repeatedly determined from the magnetic field measurements 402. The GUI is then updated to display the new position of the charger device 150 in relation to the target area 800 as the charger device 150 is moved. FIG. 8C illustrates a GUI generated on the display showing the charger device 150 is in alignment with the target 800, e.g. in the X-Y plane.

Figure 8D:
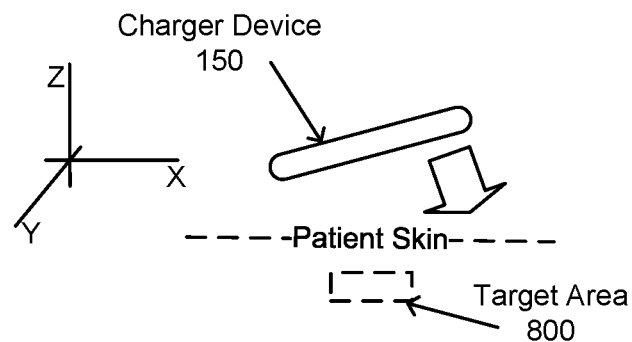

Though the charger device 150 is in alignment with the IMD 100 in the X-Y plane, it may not be aligned in the Z direction and/or the charging device 150 may have a tilt or angle with respect to the IMD 100. FIG. 8D illustrates a GUI generated on the display showing the charger device 150 is misaligned in the Z direction, e.g. the charging device 150 is beyond a distance threshold in the Z direction from the target area 800 and is at an angle or tilt with respect to the target area 150. For example, the centerline 502 or plane through the windings of the primary coil 152 must be relatively parallel to the centerline 514 or plane through the windings of the charging coil 112 in the IMD 100 as shown in FIG. 5F, e.g. less than a predetermined angle. In another example, the absolute value of the difference $Z_1$-$Z_2$ shown in FIG. 5F must be less than a predetermined threshold.

Figure 8E:
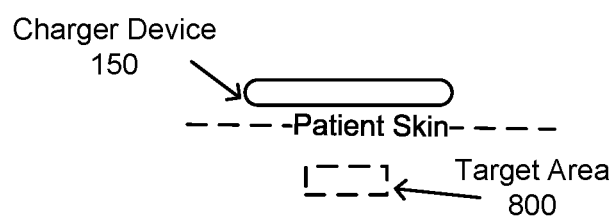

As the charger device is moved, the position of the charger device 150 is repeatedly determined from the magnetic field measurements 402. The GUI is then updated to display the new position of the charger device 150 in relation to a target area 800 as the charger device 150 is tilted and moved in the Z direction towards the patient skin. FIG. 8E illustrates a GUI generated on the display showing the charger device 150 in alignment with the target 800, e.g. in the Z direction, and that the charger device 150 and the IMD 100 are relatively parallel. The alignment of the charger device 150 may be indicated in the GUI visually, e.g. by one or more of changing a color of the target area 800 from red to green, or by an audible tone or by tactile means.

The present embodiments have an advantage over known methods based on proximity sensors. These known methods only provide information about an overall distance of the charger device 150 to the IMD 100 and are not able to determine the relative position in three dimensions of the charger device 150 to the IMD 100. In addition, these known methods are not able to determine a direction in two or three dimensions to move the charger device 150 or to angle the charger device 150 for more efficient inductive coupling with the IMD 100. In addition, the present embodiments determine a static magnetic field generated by a magnet and thus may be used during charging. The present embodiments thus provide an improved system and method for detecting alignment in three dimensions and providing more detailed instructions in two or three dimensions to a user on how to move the charger device 150 for improved alignment.

In another embodiment, a charger device 150 includes a plurality of primary coils 152 and a plurality of magnets 154. One or more of the primary coils 152 may be selected for inductive coupling to the charging coil 112 in the IMD 100. Efficient inductive coupling and charging may thus be achieved over an increased surface area of the charger device 150.

Figure 9A:
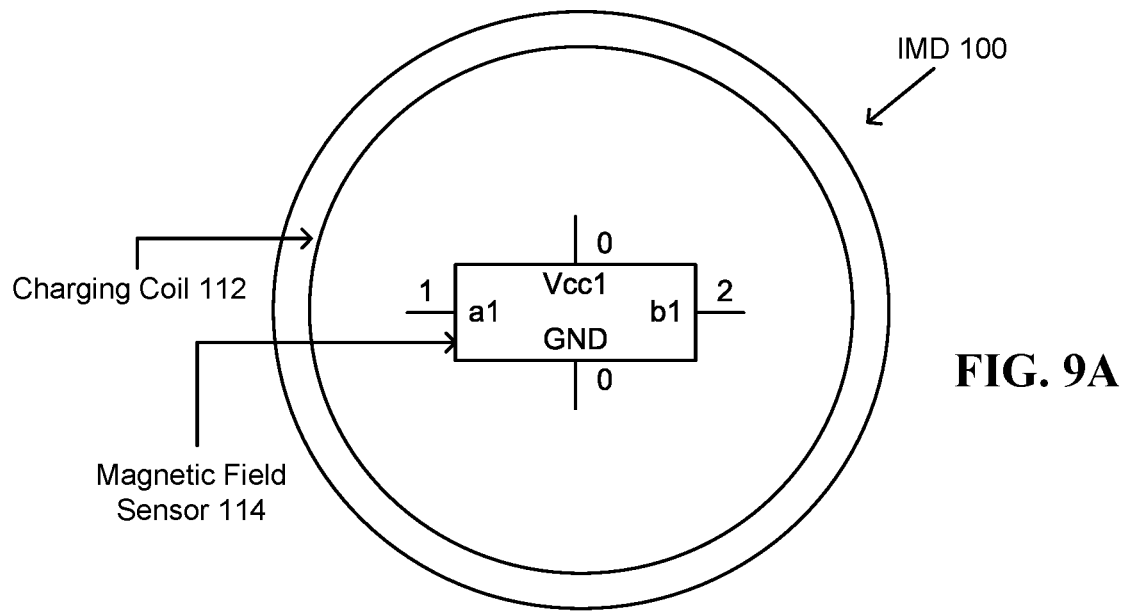
FIG. 9A is a schematic block diagram illustrating an IMD with a magnetic field sensor according to some embodiments.
Figure 9B:
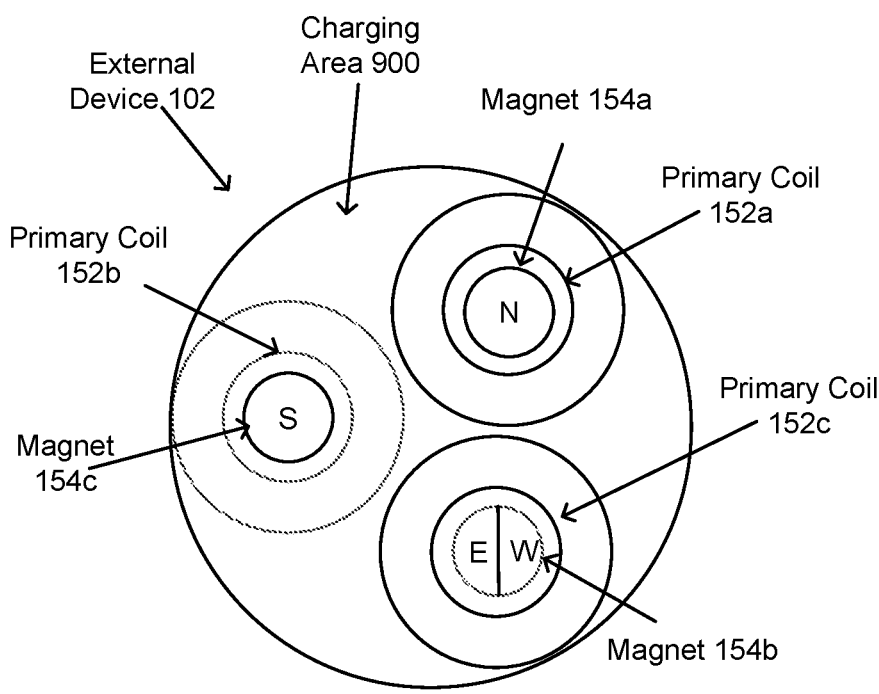
FIG. 9B is a schematic block diagrams illustrating an external device with a plurality of primary coils and magnets according to some embodiments.

FIG. 9A is a schematic block diagram illustrating this embodiment of the IMD 100 with a magnetic field sensor 114, and FIG. 9B is a schematic block diagram illustrating this embodiment of an external device 102 with a plurality of primary coils and magnets. As shown in FIG. 9A, the IMD 100 includes the charging coil 112 and magnetic field sensor 114. In an embodiment, the magnetic field sensor 114 is positioned near the charging coil 112 of the IMD 100, e.g. within 4 cm of the charging coil 112 or within a circumference of the charging coil 112. The charging coil 112 and magnetic field sensor 112 may be implemented in a same plane, e.g. on a same PCB, or in different planes on a same or different circuit boards. In FIG. 9A, the magnetic field sensor 114 is positioned at approximately a center of the charging coil 112 on a same PCB.

As shown in FIG. 9B, the charger device 150 includes a plurality of primary coils 152*a*, 152*b*, 152*c* each with an associated magnet 154*a*, 154*b*, 154*c*. Though three primary coils 152*a*-*c* are illustrated, two primary coils or additional primary coils may also be implemented. In addition, though FIG. 9B shows the primary coils 152*a-c* as non-overlapping and with open areas between the coils, the primary coils 152*a-c* may be implemented as overlapping and/or with coils weaved throughout the charging area 900. The charger device 150 may be compliant with the WPC Qi specification or with other near field wireless protocols.

The charger device 150 uses the multiple primary coils 152*a-c* to increase the surface area capable of efficient inductive coupling. With the multi-coil chargers, it is preferable to energize only one of the primary coils 152*a-c* that is best aligned with the IMD 100. In an embodiment, the magnets 154*a-c*, the magnetic field sensor 114 and the positioning application 160 are used to determine a position of the IMD 100 with respect to the plurality of primary coils 152*a-c* and select one of the primary coils 152*a-c* for inductive coupling with the IMD 100. In addition, directions to move the charger device 150 for improved alignment between the IMD 100 and the selected primary coil 154*a-c* are generated and provided to a user through visual, audible, or tactile indications.

At least one of the plurality of magnets 154*a-c* is associated with each of the plurality of primary coils 152*a-c*. The magnet 154*a-c* associated with a primary coil 152*a-c* is preferably closer to that primary coil 152*a-c* than to the other primary coils 152*a-c*, e.g. on a PCB. Thus, each magnet 154*a-c* is positioned more proximal to a different one of the plurality of primary coils 152*a-c*. For example, a magnet 154*a-c* may lay within a circumference of its associated primary coil 152*a-c*.

In one embodiment, each of the plurality of magnets 154*a-c* presents a different polarization in the charging area 900, e.g. towards the magnetic field sensor 114 in the IMD 100. For example, magnet 154*a* has a N-S polarization with the North pole positioned outwards from the charging area 900. The magnet 154*c* also has a N-S polarization but with the South pole of the magnet 154*c* positioned outwards from the charging area 900. The magnet 154*b* has an East-West polarization with both the East-West poles of the magnet 154*c* positioned facing to the charging area 900. The magnetic field sensor 114 thus has a different output of magnetic field measurements 402 depending on the proximity of each magnet 154*a-c*.

Figure 10:
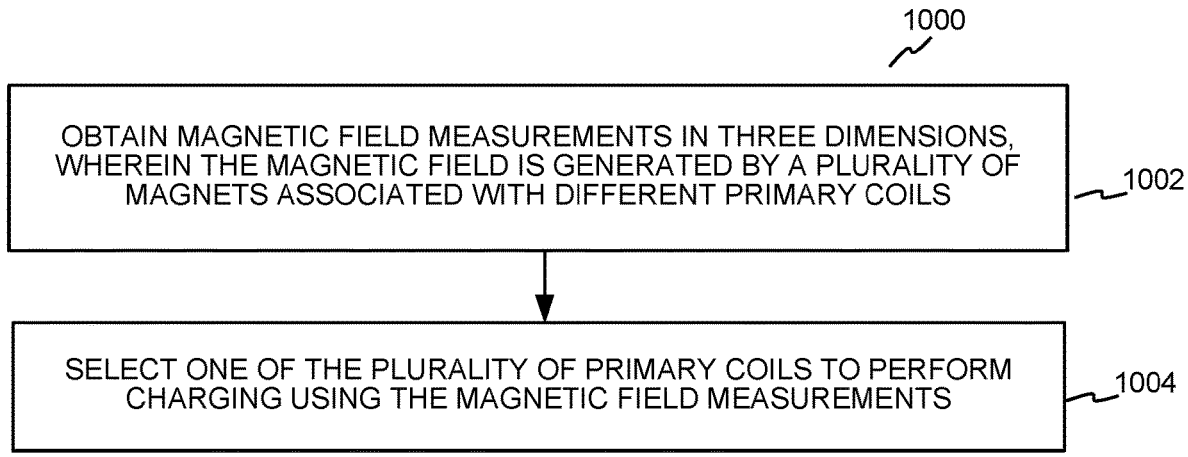
FIG. 10 is a flow diagram illustrating a method for selection of one of a plurality of primary coils in an external charger device according to some embodiments.

FIG. 10 is a flow diagram illustrating a method 1000 for selection of one of a plurality of the primary coils 152 in an external charger device 150 according to some embodiments. At 1002, the IMD 100 determines that a charger device 150 is within a predetermined range of the IMD 100 for charging. For example, the charging coil 112 of the IMD 100 may detect a voltage level, impedance load, or current that is above a predetermined proximity threshold. The proximity threshold is determined based on an output of the charging coil 112 when one or more primary coils 152 of the charger device 150 is within a range for charging of the IMD 100. In another embodiment, the magnetic field sensor 114 may detect a magnetic field with a predetermined magnetic strength that indicates a charger device 150 is within range for charging.

When the charger device 150 is detected, the IMD 100 then initiates the magnetic field sensor 114 to output measurements of the detected magnetic field. The magnetic field measurements 402 are obtained along each of three dimensions, e.g. X, Y, and Z axes at 1002. These magnetic field measurements 402 are transmitted to either the charger device 150, patient controller 170 or a user device for processing. The magnetic field sensor 114 continues to determine and output measurements of the detected magnetic field. The IMD 100 continues to transmit the magnetic field measurements 402 for processing until it receives a message to stop transmission.

The charger device 150 (or patient controller 170) uses the magnetic field measurements 402 to determine one of the plurality of primary coils 152*a-c* for charging of the IMD 100 at 1004. For example, the charger device 150 may determine a position in three dimensions of the charger device 150 with respect to the charging coil 112 in the IMD 100 using the magnetic field measurements 402. The charger device 150 then selects the one of the plurality of primary coils 152*a-c* that will provide the most efficient inductive coupling or power transfer to the charging coil 112. The selected primary coil 152 may be the closest one in linear distance based on the position of the charger device 150 or may be the primary coil 154 having the greatest overlapping surface area to the IMD 100 based on the position of the charger device 150.

In another embodiment, each of the plurality of magnets 154*a-c* has a different polarization orientation with respect to the magnetic field sensor 114. Based on the magnetic field measurements 402 in each of the different dimensions, one of the plurality of primary coils 152*a-c* may be selected. In another embodiment, each of the primary coils 152*a-c* are activated and then deactivated in turn to determine which one of the plurality of primary coils 152*a-c* provides the greatest voltage level, current, or impedance in the charging coil 112. Using one or more of these methods, one of the plurality of primary coils 152 is selected.

Figure 11:
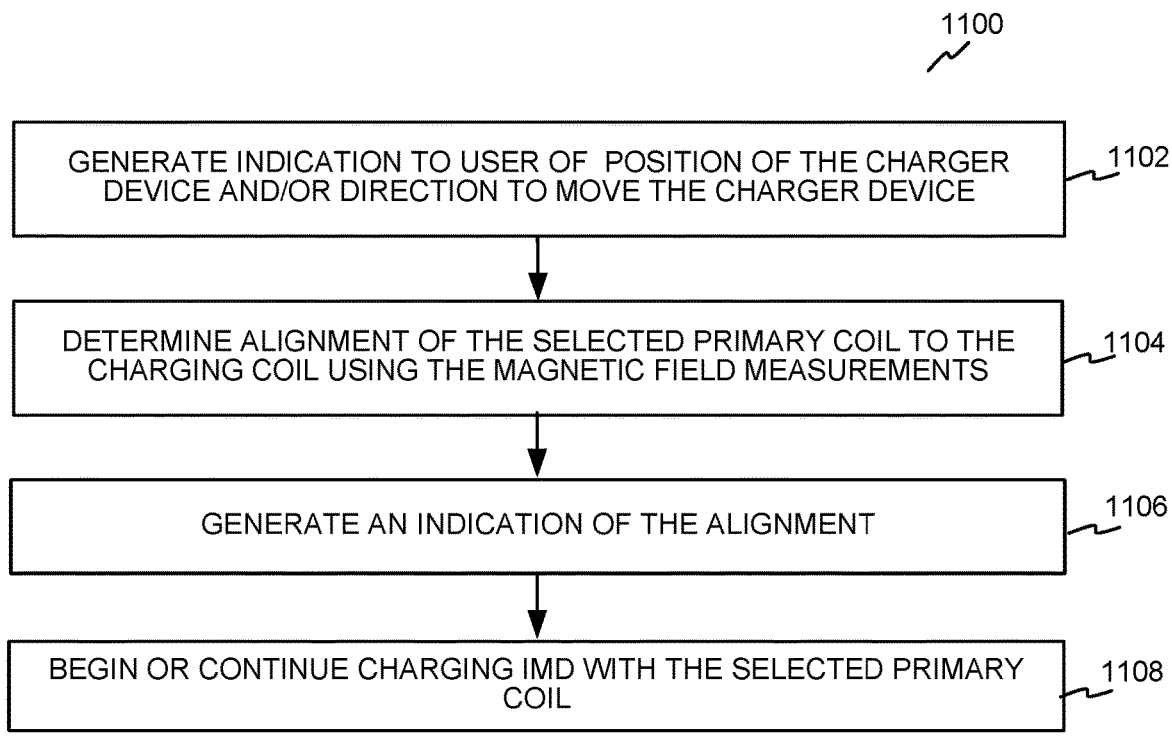
FIG. 11 is a flow diagram illustrating a method for alignment of a selected one of a plurality of primary coils to a charging coil of an IMD according to some embodiments.

FIG. 11 is a flow diagram illustrating a method 1100 for alignment of the selected one of the plurality of primary coils 152 to the charging coil 112 of the IMD 100 according to some embodiments. When the selected primary coil 152 of the charger device 150 is not properly aligned with the charging coil 112 of the IMD 100, the magnetic field measurements 402 are used to determine a position of the charger device 150 with respect to the selected charging coil 112. An indication is then generated of a position of the charger device 150 or a direction to move the charger device 150 for improved alignment at 1102. The position of the charger device 150 and/or the direction to move the charger device 150 is provided to a user. A user may thus be informed to move the charger device 150 along one or more of the X, Y or Z directions. For example, an indication may be generated to move the charger device 150 along the Z axis (e.g. to move the charger device 150 closer or further from the patient's skin). In another example, an indication may be generated to move the charger device 150 in an X or Y direction or in both an X and Y direction. In another example, an indication may be generated to angle or tilt a portion of the charger device 150 towards or away from the skin of the patient.

The magnetic field sensor 114 continues to output measurements of the detected magnetic field. The position of the charger device 150 and/or indications to move the charger device 150 are continually generated for the user until an alignment of the charger device 150 with the selected primary coil 152 is determined at 1104. Alignment of the charger device 150 occurs when the charger device 150 is in a relative position to the selected primary coil 152 for efficient inductive coupling.

The alignment of the charger device 150 is indicated to the user at 1106. The user should then stop movement of the charger device 150 and hold or otherwise secure the charger device 150 in the aligned position. The charger device 150 may then begin or continue charging using the selected primary coil 152 at 1108.

In another embodiment, a charger device 150 includes a plurality of magnets 154 that are not associated with a particular primary coil 152 but are spaced apart within the charger device 150. Moreover, the IMD 100 includes a plurality of magnetic field sensors 114 positioned apart within the IMD 114. The plurality of magnetic field sensors 114 detect the magnetic field generated by the plurality of magnets 154. The measurements from each of the plurality of magnetic field sensors 154 are used to determine a position of the charger device 150 relative to the IMD 100 in three dimensions. As such, the position of the charger 150 may be aligned with the IMD 100 independent of the number of primary coils and coil shapes.

Figure 12A:
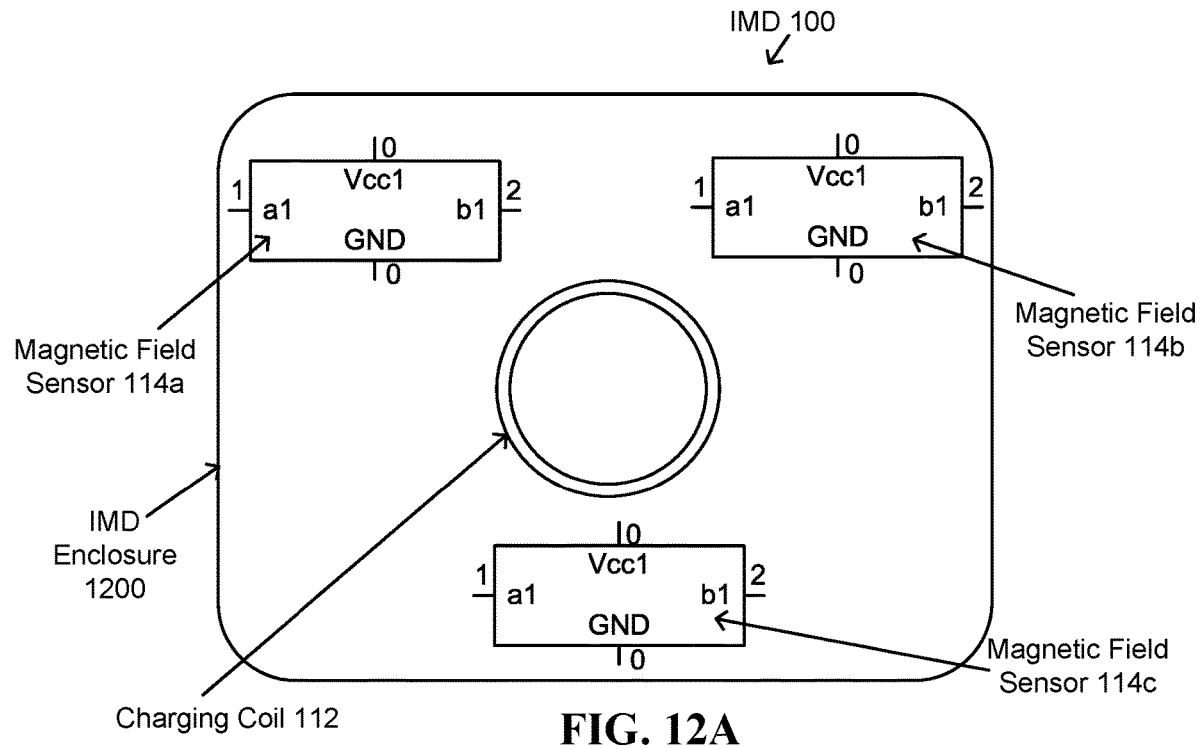
FIG. 12A is a schematic block diagram illustrating an embodiment of an IMD with a plurality of magnetic field sensors according to some embodiments.
Figure 12B:
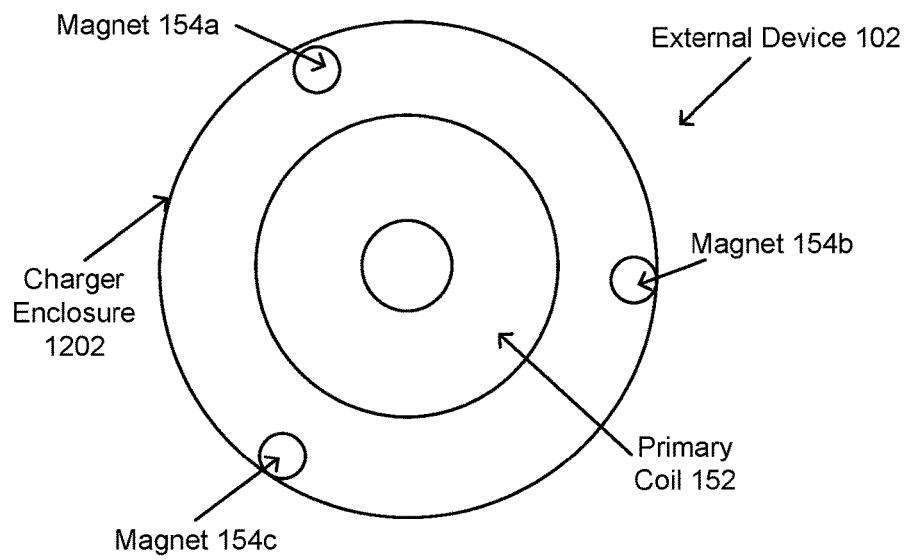
FIG. 12B is a schematic block diagram illustrating an external device with a plurality of magnets and one or more primary coils according to some embodiments.

FIG. 12A is a schematic block diagram illustrating this embodiment of the IMD with a plurality of magnetic field sensors 114*a-c*, and FIG. 12B is a schematic block diagram illustrating an external device 102 with a plurality of magnets 154*a-c* and one or more primary coils 152. As shown in FIG. 12A, the IMD 100 includes a plurality of magnetic field sensors 114*a*, 114*b*, 114*c*. The magnetic field sensors 114*a-c* are not associated with a particular charging coil 112 but are positioned apart within the IMD enclosure 1200. Preferably, the magnetic field sensors 114*a-c* are positioned approximately equidistance apart along a perimeter of the IMD enclosure 1200. In this example, three magnetic field sensors 114*a-c* are illustrated but a different number may be implemented, such as two, four or five.

In the example of FIG. 12B, the external device 102 is a charger device 150 having a plurality of magnets 154*a*, 154*b*, 154*c* positioned around an edge of the charger enclosure 1202. The plurality of magnets 154*a-c* are not associated with a particular primary coil 152. Though three magnets 154*a-c* are illustrated, a different number may be implemented, such as two, four or five, that may or may not be the same number of magnetic field sensors 114*a-c*. In addition, though one primary coil 152 is shown, a plurality of primary coils 152 may be implemented as well. In one embodiment, each of the plurality of magnets 154*a-c* has a different polarization orientation with respect to a charging pad of the charger enclosure 1202.

Figure 13:
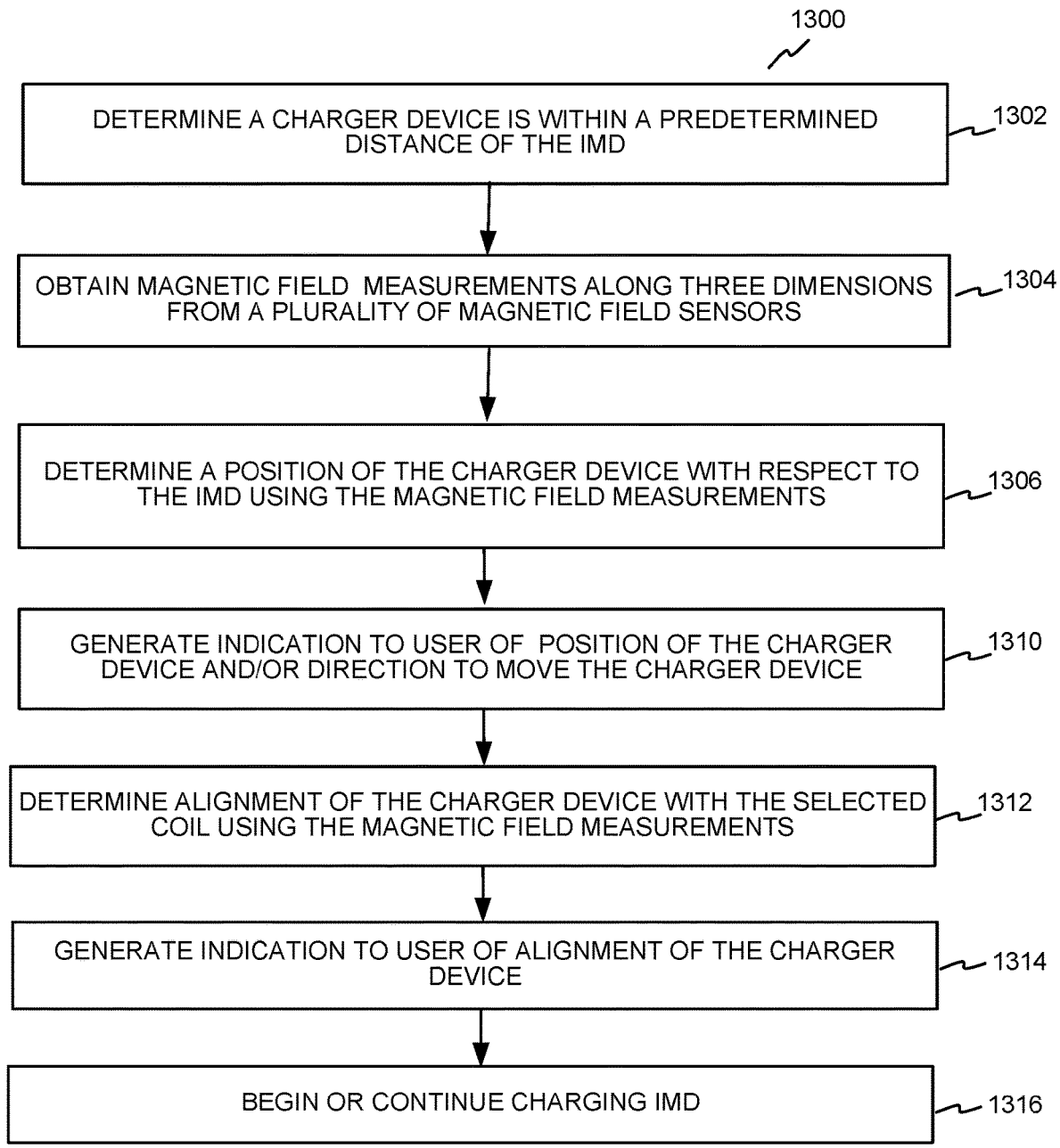
FIG. 13 is a flow diagram illustrating a method for alignment of an external device to an IMD using a plurality of magnetic field sensors according to some embodiments.

FIG. 13 is a flow diagram illustrating a method 1300 for alignment of an external device 102 to an IMD 100 using a plurality of magnetic field sensors 114*a-c* according to some embodiments. In use, one or more of the magnetic field sensors 114*a-c* detects a static magnetic field strength that is above a predetermined threshold indicating that at least one primary coil 152 of the charger device 150 is within a predetermined distance of the IMD 100 at 1302. In another embodiment, the charging coil 112 of the IMD 100 may detect a voltage level, flow of current or impedance above a predetermined threshold indicating that the charger device 150 is within a predetermined distance for charging. In another embodiment, other proximity sensors may be implemented that detect the proximity of the charger device 150 to the IMD 100.

When the proximity of the charger device 150 is detected, the IMD 100 initiates the plurality of magnetic field sensors 114*a-c* to output measurements of the detected magnetic field in three dimensions, e.g. along the X, Y, and Z axes at 1304. The magnetic field sensors 114*a-c* continue to periodically output the measurements, e.g. at one or two times per second, until indicated by the IMD 100 to stop. The magnetic field measurements 402 are then obtained using the plurality of magnetic field sensors 114*a-c* at 1304.

The magnetic field measurements may be processed by the IMD 100 or may be transmitted to the charger device 150 or to the patient controller 170 or to another user device for processing. The magnetic field measurements from the plurality of magnetic field sensors 114*a-c* are then used to determine a position of the charger device 150 with respect to the IMD 100 at 1306. Based on the position, a misalignment of the charger device 150 to the IMD 100 is determined. For example, the position of the charger device 150 is determined when the primary coil 152 and charging coil 112 achieve efficient inductive coupling. If the position of the charger device 150 is not within this position, the charger device 150 is not aligned with the IMD 100. In another example, the magnetic field measurement 402 along the X, Y, and Z axes for each of the plurality of magnetic field sensors 114*a-c* may be compared to predetermined thresholds that were determined during an efficient inductive coupling. When the thresholds are not met, the charger device 150 is not aligned with the IMD 100.

When misaligned, the magnetic field measurements 402 are used to generate an indication to a user of a position of the charger device 150 with respect to the IMD 100 and/or a direction to move the charger device 150 for improved alignment at 1310. The position of the charger device 150 and/or the direction to move the charger device 150 may be provided in two or three dimensions. For example, an indication may be generated to move the charger device 150 along the Z axis. In another example, an indication may be generated to move the charger device 150 in an X or Y direction or in both an X and Y direction. In another example, an indication may be generated to angle or tilt a portion of the charger device 150 towards the skin of the patient.

The indications to the user of the position of the charger device 150 and/or directions to move the charger device 150 are continued until an alignment of the charger device 150 with the IMD is determined at 1312. Alignment of the charger device 150 occurs when the primary coil 152 of the charger device 150 is within a predetermined linear distance and position relative to the charging coil 112 for efficient inductive coupling. The alignment of the charger device 150 is indicated to the user at 1314. The user should then stop movement of the charger device 150 and hold or otherwise secure the charger device 150 in the aligned position. The charger device 150 may then begin or continue charging at 1316.

Figure 14:
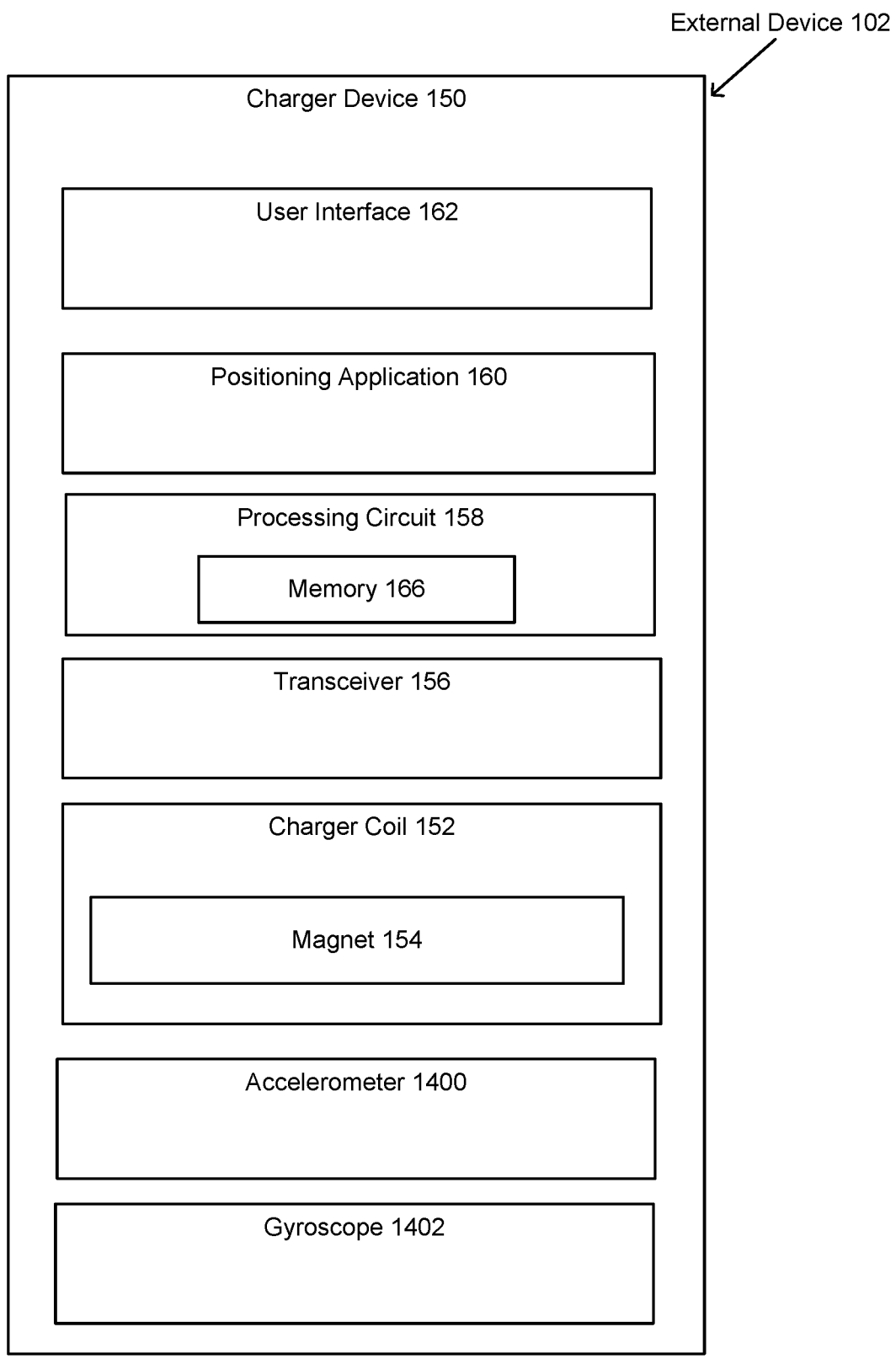
FIG. 14 is a schematic block diagram illustrating another embodiment of a charger device according to some embodiments.

FIG. 14 is a schematic block diagram illustrating another embodiment of the charger device 150. In this embodiment, the charger device 150 includes an accelerometer 1400 and/or a gyroscope 1402. For example, the accelerometer 1400 may be a three-axis accelerometer that measures linear acceleration in up to three-dimensions (for example, X, Y, Z axes). The gyroscope 1402 may be a three-axis MEMS gyroscope that measures rotational data, such as rotational movement and/or angular velocity, in up to three-dimensions (for example, yaw, pitch, and roll). The positioning application 160 receives motion data from the accelerometer 1400 and/or gyroscope 1402 and uses the motion data to help determine the position of the charger device 150.

Figure 15:
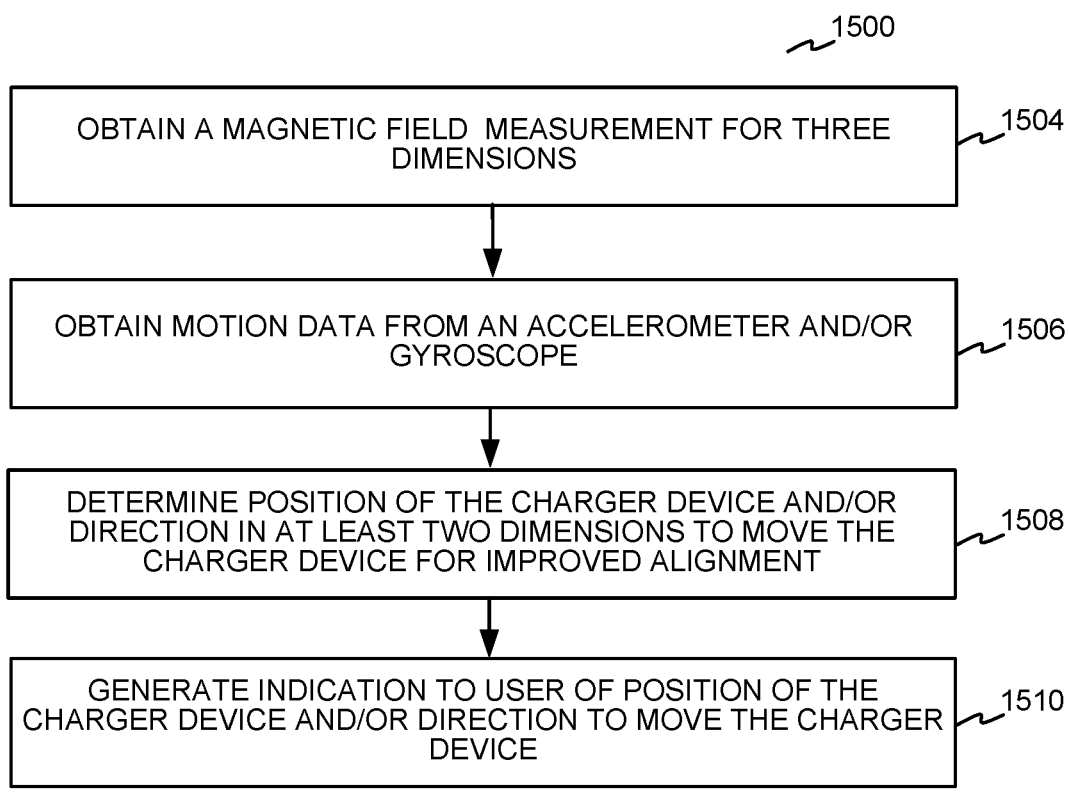
FIG. 15 is a flow diagram illustrating a method for alignment of an external device to an IMD using magnetic field measurements and motion data according to some embodiments.

FIG. 15 is a flow diagram illustrating a method 1500 for alignment of an external device 102 to an IMD 100 using magnetic field measurements 402 and motion data according to some embodiments. The magnetic field measurements 402 are obtained in three dimensions, e.g. for the X, Y and Z axes, at 1504. In addition, motion data is obtained from an accelerometer 1400 and/or gyroscope 1402 or another similar device, at 1506. The motion data includes, e.g., linear acceleration in up to three-dimensions (for example, X, Y,Z axes), e.g. from the accelerometer 1400 or rotational data, e.g. such as rotational movement and/or angular velocity, in up to three-dimensions (for example, yaw, pitch, and roll) from the gyroscope 1402.

The position of the charger device 150 with respect to the IMD and a direction to move the charger device 150 for improved alignment with the IMD is determined using the magnetic field measurements 402 and the motion data at 1508. For example, the motion data may be processed to determine that the charger device 150 is oriented vertically, horizontally or at an angle with respect to the ground. In another example, the motion data may be processed to determine a rotational movement of the charger device 150 as it is tilted or angled towards a patient. The motion data may thus help provide further information on the orientation and position of the charger device 150.

An indication is generated of the position of the charger device 150 and/or the direction to move the charger device 150 in two or three dimensions at 1510. A user may thus be informed to move the charger device 150 along one or more of the X, Y or Z directions or to rotate or tilt the charger device 150. For example, an indication may be generated to move or tilt the charger device 150 along the Z axis. In another example, an indication may be generated to move the charger device 150 in an X or Y direction or in both an X and Y direction. The motion data along with the magnetic field measurements may be used to provide the instructions on how to move the charger device 150 to improve alignment with the IMD 100. The motion data may also be used with the magnetic field measurements 402 to determine a position of the charger device 150 as it is moved to improve the alignment with the IMD 100.

Figure 16:
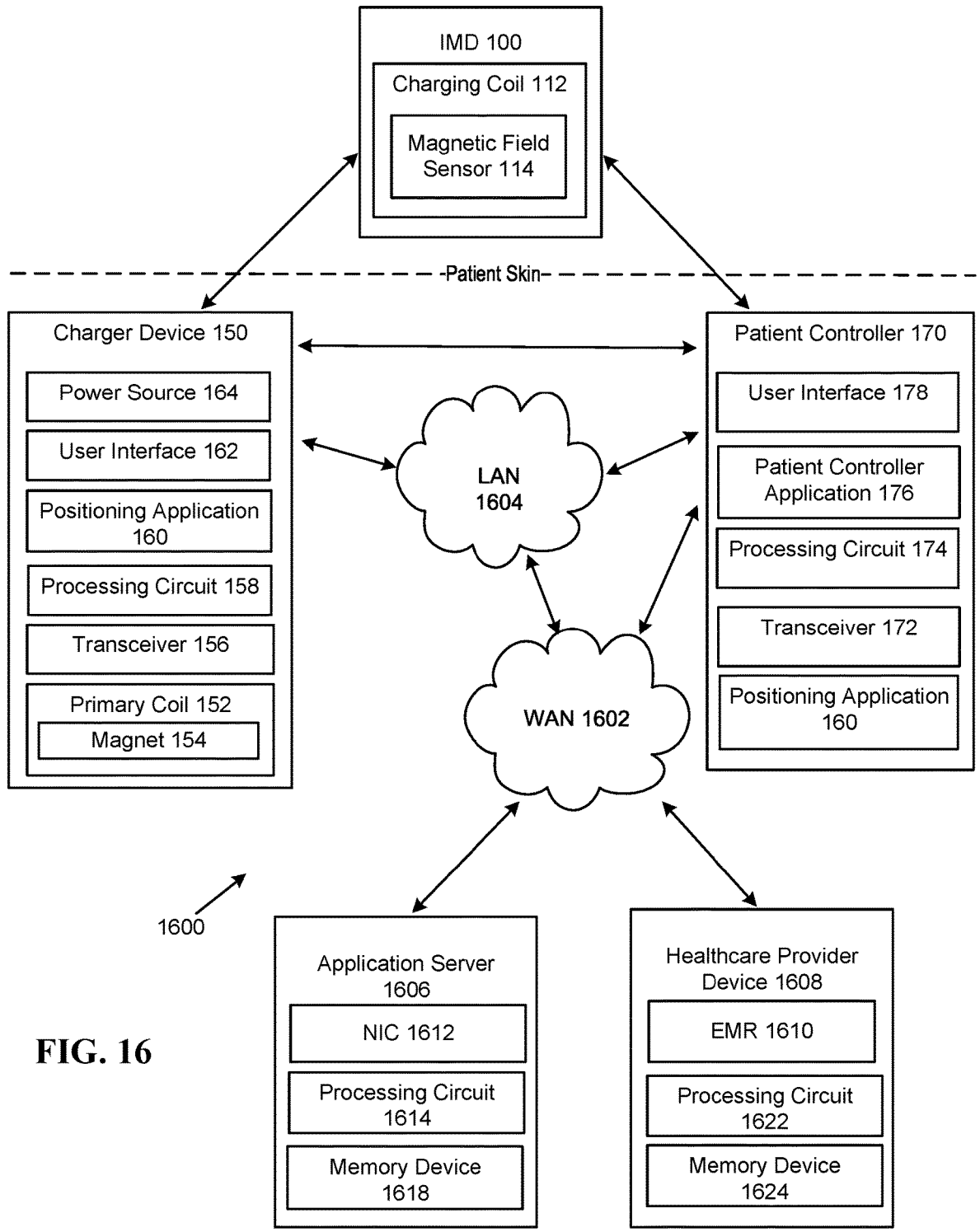
FIG. 16 is a schematic block diagram of an exemplary network in which a charger device and a patient controller may operate according to some embodiments.

FIG. 16 is a schematic block diagram of an exemplary network 1600 in which the charger device 100 and patient controller 170 may operate. The exemplary network 1600 includes one or more networks that are communicatively coupled, e.g., such as a wide area network (WAN) 1602 and a local area network (LAN) 1604. The WAN 1602 may include a wireless or wired WAN, such as a 4G or 5G cellular network, service provider network, Internet, etc. The WLAN 1602 may include a wired or wireless LAN and operate inside a home or enterprise environment. Other networks may be included to communicatively couple the devices, such as edge networks, metropolitan area networks, satellite networks, etc.

The IMD 100 may communicate using a wireless protocol to one or more of the charger device 150 or the patient controller 170. The patient controller 170 and the charger device 150 may communicate directly using Bluetooth or other wireless or wired protocol or communicate indirectly through the WLAN. Though the charger device 150 and the patient controller 170 are shown as separate devices, the charger device 150 may be incorporated into the patient controller 170. The patient controller 170 and/or the charger device 150 may be implemented in a user device, such as a smart phone, laptop, desktop, smart tablet, smart watch, or other electronic device.

In an embodiment, the charger device 150 and/or patient controller 170 may communicate to an application server 1606. The application server 1606 may provide software updates to the charger device 150 and/or the patient controller 170. The charger device 150 and/or the patient controller 170 may provide operational data and/or patient data to the application server 1606. The application server 1606 includes a network interface circuit 1612 and a server processing circuit 1614. The network interface circuit (NIC) 1612 includes an interface for wireless and/or wired network communications with one or more of the exemplary networks in the network 1600. The NIC 1612 may also include authentication capability that provides authentication prior to allowing access to some or all of the resources of the application server 1606. The NIC 1612 may also include firewall, gateway, and proxy server functions. The application server 1606 also includes a processing circuit 1614 and a memory device 1618. For example, the memory device 1618 is a non-transitory, processor readable medium that stores instructions and/or data which when executed or processed by the processing circuit 1614, causes the application server 1606 to perform one or more functions described herein.

In another embodiment, the charger device 150 and/or patient controller 170 may communicate to a local or remote healthcare provider device 1608, e.g. in a physician's office, clinic, or hospital. The healthcare provider device 1608 may store patient or therapeutic information in an electronic medical record (EMR) 1610 associated with the user of the IMD 100. The healthcare provider device 1608 also includes a processing circuit 1622 and a memory device 1624. For example, the memory device 1624 is a non-transitory, processor readable medium that stores instructions and/or data which when executed by the processing circuit 1622, causes the healthcare provider device 1608 to perform one or more functions described herein.

A processing circuit as described herein includes one or more processing devices on one or more printed circuit boards, including one or more of a microprocessor, microcontroller, digital signal processor, video graphics processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory device is a non-transitory memory device and may be an internal memory or an external memory to the processing circuit, and the memory may be a single memory device or a plurality of memory devices. The memory device may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition, or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied, or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A system for wirelessly providing power to an implantable medical device (IMD), comprising:
    an external charger device, including:
        a primary coil configured to wirelessly transfer power to a charging coil in the IMD;
        at least one external magnet having a static magnetic field, wherein the at least one external magnet is positioned in proximity to the primary coil;
    an external user device, including:
        a transceiver configured to communicate with the IMD using a wireless protocol;
        at least one processing circuit including at least one processing device and at least one memory device, wherein the at least one memory device stores instructions that, when executed by the at least one processing device, causes the external user device to:
            obtain, from a transceiver within the IMD, a magnetic field measurement of the static magnetic field within the IMD of the at least one external magnet along each of three axes, wherein each of the magnetic field measurements is a value proportional to the static magnetic field along one of the three axes detected in the IMD; and
            determine a relative position in three dimensions of the external charger device to the IMD using the magnetic field measurements.

2. The system of claim 1, wherein the at least one memory device stores instructions that when executed by the at least one processing device, causes the external user device to:
    determine a direction to move the external charger device with respect to a patient's skin to improve alignment of the primary coil in the external charger device to the charging coil in the IMD.

3. The system of claim 2, wherein the at least one memory device stores instructions that when executed by the at least one processing device, causes the external user device to:
    generate an indication to move the external charger device in the determined direction, wherein the indication is a visual graphical user interface (GUI) or an audible indication.

4. The system of claim 1, wherein the at least one memory device stores instructions that when executed by the at least one processing device, causes the external user device to:
    determine a direction to tilt a portion of the external charger device with respect to a patient's skin so that the primary coil in the external charger device and the charging coil in the IMD are relatively more parallel.

5. The system of claim 4, wherein the at least one memory device stores instructions that when executed by the at least one processing device, causes the external user device to:
    generate an indication to tilt the portion of the external charger device with respect to the patient's skin, wherein the indication is a visual graphical user interface (GUI) or an audible indication.

6. The system of claim 1, wherein the at least one memory device stores instructions that when executed by the at least one processing device, causes the external user device to:
    determine to move the external charger device in closer proximity to a patient's skin so that a relative distance from a center of the primary coil in the external charger device and a center of the charging coil in the IMD is decreased.

7. The system of claim 6, wherein the at least one memory device stores instructions that when executed by the at least one processing device, causes the external user device to:
generate an indication to move the external charger device in closer proximity to a patient's skin, wherein the indication is a visual graphical user interface (GUI) or an audible indication.

8. The system of claim 1, wherein the at least one memory device stores instructions that when executed by the at least one processing device, causes the external user device to:
determine an alignment of the primary coil to the charging coil when the relative positions in each of three dimensions of the external device to the IMD are within predetermined distance thresholds.

9. The system of claim 1, wherein the at least one memory device stores instructions that when executed by the at least one processing device, causes the external user device to:
determine an alignment of the primary coil in the external charger device to the charging coil in the IMD when the magnetic field measurements along the three axes are within predetermined thresholds.

10. An external system for wirelessly providing power to an implantable medical device (IMD), comprising:
a plurality of primary coils configured to wirelessly transfer power to a charging coil in the IMD;
a plurality of magnets, wherein each magnet of the plurality of magnets is positioned more proximal to a different one of the plurality of primary coils;
a transceiver configured to communicate with the IMD using a wireless protocol; and
at least one processing circuit configured to:
obtain from the IMD magnetic field measurements in each of three dimensions, wherein each of the magnetic field measurements is a value proportional to a magnetic field detected by at least one magnetic field sensor in the IMD, wherein the magnetic field is generated by one or more of the plurality of magnets in the external system so that a different output of magnetic field measurements in each of three dimensions is obtained depending on a proximity of each magnet of the plurality of magnets to the at least one magnetic field sensor;
select one of the plurality of primary coils for wireless transfer of power to the charging coil in the IMD; and
determine a relative position in three dimensions of the external system to the IMD using the magnetic field measurements.

11. The external system of claim 10, wherein the at least one processing circuit is configured to:
select the one of the plurality of primary coils for wireless transfer of power to the charging coil in the IMD using at least the magnetic field measurements in each of three dimensions.

12. The external system of claim 11, wherein the at least one processing circuit is configured to select the one of the plurality of primary coils by:
selecting the one of the plurality of primary coils having a greater overlapping surface area to the charging coil in the IMD based on the relative position in three dimensions of the external device to the IMD.

13. The external system of claim 10, wherein the at least one processing circuit is configured to:
determine a direction to move the external device to improve alignment of the selected one of the plurality of primary coils to the charging coil in the IMD.

14. The external system of claim 13, wherein the at least one processing circuit is configured to:
determine a direction to angle the external device so that the selected one of the plurality of primary coils and the charging coil are relatively more parallel.

* * * * *